US010357574B2

United States Patent
Hilderbrand et al.

(10) Patent No.: US 10,357,574 B2
(45) Date of Patent: Jul. 23, 2019

(54) OPTICAL SENSOR CONJUGATES FOR DETECTING REACTIVE OXYGEN AND/OR REACTIVE NITROGEN SPECIES IN VIVO

(71) Applicant: The General Hospital Corporation, Boston, MA (US)

(72) Inventors: Scott A. Hilderbrand, Swampscott, MA (US); Ralph Weissleder, Peabody, MA (US); Peter Panizzi, Auburn, AL (US); Jason R. McCarthy, Townsend, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/583,197

(22) Filed: May 1, 2017

(65) Prior Publication Data
US 2017/0368202 A1 Dec. 28, 2017

Related U.S. Application Data

(63) Continuation of application No. 13/700,255, filed as application No. PCT/US2011/038903 on Jun. 2, 2011, now Pat. No. 9,636,423.

(60) Provisional application No. 61/350,772, filed on Jun. 2, 2010.

(51) Int. Cl.
*A61K 49/00* (2006.01)

(52) U.S. Cl.
CPC ........ *A61K 49/003* (2013.01); *A61K 49/0028* (2013.01); *A61K 49/0054* (2013.01); *A61K 49/0093* (2013.01)

(58) Field of Classification Search
CPC ............ A61K 49/0028; A61K 49/0054; A61K 49/003; A61K 49/0093
See application file for complete search history.

(56) References Cited

U.S. PATENT DOCUMENTS

| | | | |
|---|---|---|---|
| 4,284,696 A * | 8/1981 | Ishida | G03G 5/12 106/31.2 |
| 5,262,176 A | 11/1993 | Palmacci et al. | |
| 5,492,814 A | 2/1996 | Weissleder | |
| 5,663,042 A * | 9/1997 | Grieve | C07F 7/21 430/203 |
| 7,060,121 B2 | 6/2006 | Lin et al. | |
| 7,232,474 B2 | 6/2007 | Bouvrette et al. | |
| 7,375,234 B2 | 5/2008 | Sharpless et al. | |
| 2005/0250214 A1 | 10/2005 | Gee | |
| 2005/0249668 A1 | 11/2005 | Weissleder et al. | |
| 2007/0141658 A1 | 6/2007 | Chang | |
| 2008/0095699 A1 | 4/2008 | Zheng | |
| 2008/0166706 A1 | 7/2008 | Zhang et al. | |
| 2010/0055040 A1 | 3/2010 | Periasamy et al. | |

FOREIGN PATENT DOCUMENTS

WO    WO 2000/061191    10/2000

OTHER PUBLICATIONS

Kamogawa, H. et al., J. Polymer Sci., A., 1986, 24, p. 1565-1575.*
Abe et al., "Correlation of in vitro autofluorescence endoscopy images with histopathologic findings in stomach cancer," Endoscopy, 32(4):281-286 (Apr. 2000).
Alfano et al., "Advances in optical imaging of biomedical media," Ann. NY Acad. Sci., 820:248-270 (May 30, 1997).
Aratani et al., "Severe impairment in early host defense against Candida albicans in mice deficient in myeloperoxidase," Infect Immun., 67(4):1828-36 (Apr. 1999).
Boas et al., "Scattering of diffuse photon density waves by spherical inhomogeneities within turbid media: analytic solution and applications," Proc. Natl. Acad. Sci. USA, 91(11):4887-4891 (May 24, 1994).
Boppart et al., "Noninvasive assessment of the developing Xenopus cardiovascular system using optical coherence tomography," Proc. Natl. Acad. Sci. USA, 94(9):4256-4261 (Apr. 19, 1997).
Chance, "Near-infrared images using continuous, phase-modulated, and pulsed light with quantitation of blood and blood oxygenation," Ann. NY Acad. Sci., 838:29-45 (Feb. 9, 1998).
Cheng and Boas "Diffuse optical reflection tomography using continuous wave illumination," Optics Express, 3(3):118-123 (Aug. 3, 1998).
Dellian et al., "Vascular permeability in a human tumour xenograft: molecular charge dependence," Br. J Cancer 82(9):1513-1518 (May 2000).
Fukumura et al., "Tumor induction of VEGF promoter activity in stromal cells," Cell, 94(6):715-725 (Sep. 18, 1998).
Gahlen et al., "Spectrometry supports fluorescence staging laparoscopy after intraperitoneal aminolaevulinic acid lavage for gastrointestinal tumours," J Photochem. Photobiol. B, 52(1-30):131-135 (Sep.-Oct. 1999).
Gomes et al., "Use of Fluorescence Probes for Detection of Reactive Nitrogen Species: A Review," Journal of Fluorescence 16(1):119-139 (2006).
Gonzalez et al., "Characterization of psoriasis in vivo by reflectance confocal microscopy," J. Med., 30(5-6):337-356 (1999).
Halbreich et al., "Biomedical applications of maghemite ferrofluid," Biochimie, 80(5-6):379-90 (May-Jun. 1998).
Harisinghani et al., "Utility of a new bolus-injectable nanoparticle for clinical cancer staging," Neoplasia, 9(12):1160-5 (Dec. 2007).
International Preliminary Report on Patentability in International Application No. PCT/US2011/038903, dated Dec. 4, 2012, 6 pages.
International Search Report and Written Opinion from International Application No. PCT/US2011/038903 dated Feb. 2, 2012, 10 pgs.
Izuishi et al., "Detection of bile duct cancer by autofluorescence cholangioscopy: a pilot study," Hepatogastroenterol., 46(26):804-807 (Mar.-Apr. 1999).
Josephson et al., "High-efficiency intracellular magnetic labeling with novel superparamagnetic-Tat peptide conjugates," Bioconjug. Chem., 10(2):186-91 (Mar.-Apr. 1999).
Koch et al., "Uptake and metabolism of a dual fluorochrome Tat-nanoparticle in HeLa cells," Bioconjug Chem., 14(6):1115-21 (Nov.-Dec. 2003).

(Continued)

*Primary Examiner* — Michael G. Hartley
*Assistant Examiner* — Leah H Schlientz
(74) *Attorney, Agent, or Firm* — Fish & Richardson P.C.

(57) ABSTRACT

The present invention provides methods and compositions based on optical sensor conjugates that are useful for detecting reactive oxygen, reactive nitrogen, or both species that are a direct result of inflammation caused by tissue damage.

10 Claims, 8 Drawing Sheets

(56) References Cited

OTHER PUBLICATIONS

Korlach et al., "Characterization of lipid bilayer phases by confocal microscopy and fluorescence correlation spectroscopy," Proc. Natl. Acad. Sci. USA, 96(15):8461-8466, (Jul. 20, 1999).

Lacza et al., "The novel red-fluorescent probe DAR-4M measures reactive nitrogen species rather than NO," Journal of Pharmacological and Toxicological Methods 52: 335-340 (2005).

Lee et al., Biomaterials, 2008, 29(35):4709-4718.

Major et al., "In vivo fluorescence detection of ovarian cancer in the NuTu-19 epithelial ovarian cancer animal model using 5-aminolevulinic acid (ALA)," Gynecol. Oncol., 66(1):122-132 (Jul. 1997).

Monsky et al., "Augmentation of transvascular transport of macromolecules and nanoparticles in tumors using vascular endothelial growth factor," Cancer Res. 59(16):4129-4135 (Aug. 15, 1999).

Mycek et al., "Colonic polyp differentiation using time-resolved autofluorescence spectroscopy," Gastrointest. Endosc., 48(4):390-394 (Oct. 1998).

Nagano, "Bioimaging Probes for Reactive Oxygen Species and Reactive Nitrogen Species," J. Clin. Biochem. Nutr. 45: 111-124 (2009).

Nahrendorf et al., "Factor XIII deficiency causes cardiac rupture, impairs wound healing, and aggravates cardiac remodeling in mice with myocardial infarction," Circulation, 113(9):1196-202 (Mar. 7, 2006).

Nahrendorf et al., "Nanoparticle PET-CT imaging of macrophages in inflammatory atherosclerosis," Circulation, 117(3):379-87 (Jan. 22, 2008).

Nahrendorf et al., "The healing myocardium sequentially mobilizes two monocyte subsets with divergent and complementary functions," J Exp Med., 204(12):3037-47 (Nov. 26, 2007).

Ntziachristos et al., "Concurrent MRI and diffuse optical tomography of breast after indocyanine green enhancement," Proc. Natl. Acad. Sci. USA, 97(6):2767-2772 (Mar. 14, 2000).

Panizzi et al., J. Am. Chem. Soc., 2009, 131(43):15739-15744.

Poulsen et al., "Horseradish peroxidase embedded in polyacrylamide nanoparticles enables optical detection of reactive oxygen species," Analytical Biochemistry 366:29-36 (2007).

Qian et al., "In vivo tumor targeting and spectroscopic detection with surface-enhanced Raman nanoparticle tags," Nat. Biotechnol., 26(1):83-90 (Jan. 2008).

Rajadhyaksha et al., "In vivo confocal scanning laser microscopy of human skin: melanin provides strong contrast," J Invest Dermatol., 104(6):946-952 (1995).

Sanvicens and Marco, "Multifunctional nanoparticles—properties and prospects for their use in human medicine," Trends Biotech., 26(8):425-433 (Aug. 2008).

Siegel et al., "Design and evaluation of a continuous-wave diffuse optical tomography system," Optics Express, 4(8):287-298 (Apr. 12, 1999).

Stepp et al., "Fluorescence endoscopy of gastrointestinal diseases: basic principles, techniques, and clinical experience," Endoscopy, 30(4):379-386 (May 1998).

Tearney et al., "In vivo endoscopic optical biopsy with optical coherence tomography," Science, 276(5321):2037-2039 (Jun. 27, 1997).

Ward, "New laser techniques for diagnosis and treatment of deep-seated brain lesions," J Laser Appl., 10(5):224-228 (Oct. 1998).

Wu et al., ACS Nano, 2008, 2(11):2401-9.

Yasmin et al., "Generation of peroxynitrite contributes to ischemia-reperfusion injury in isolated rat hearts," Cardiovasc Res., 33(2):422-32 (Feb. 1997).

\* cited by examiner

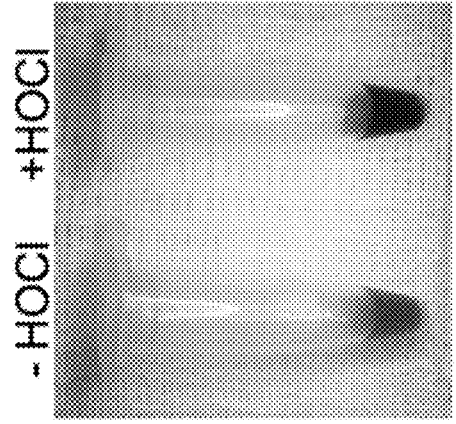
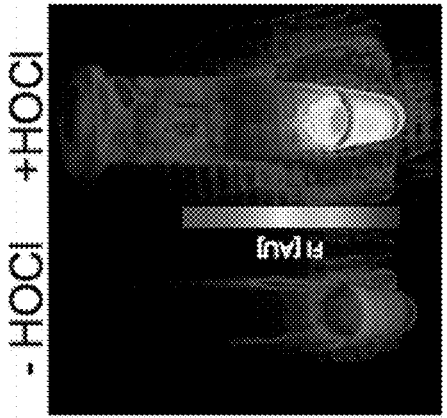
FIG. 2A
FIG. 2B
FIG. 2C
FIG. 2D

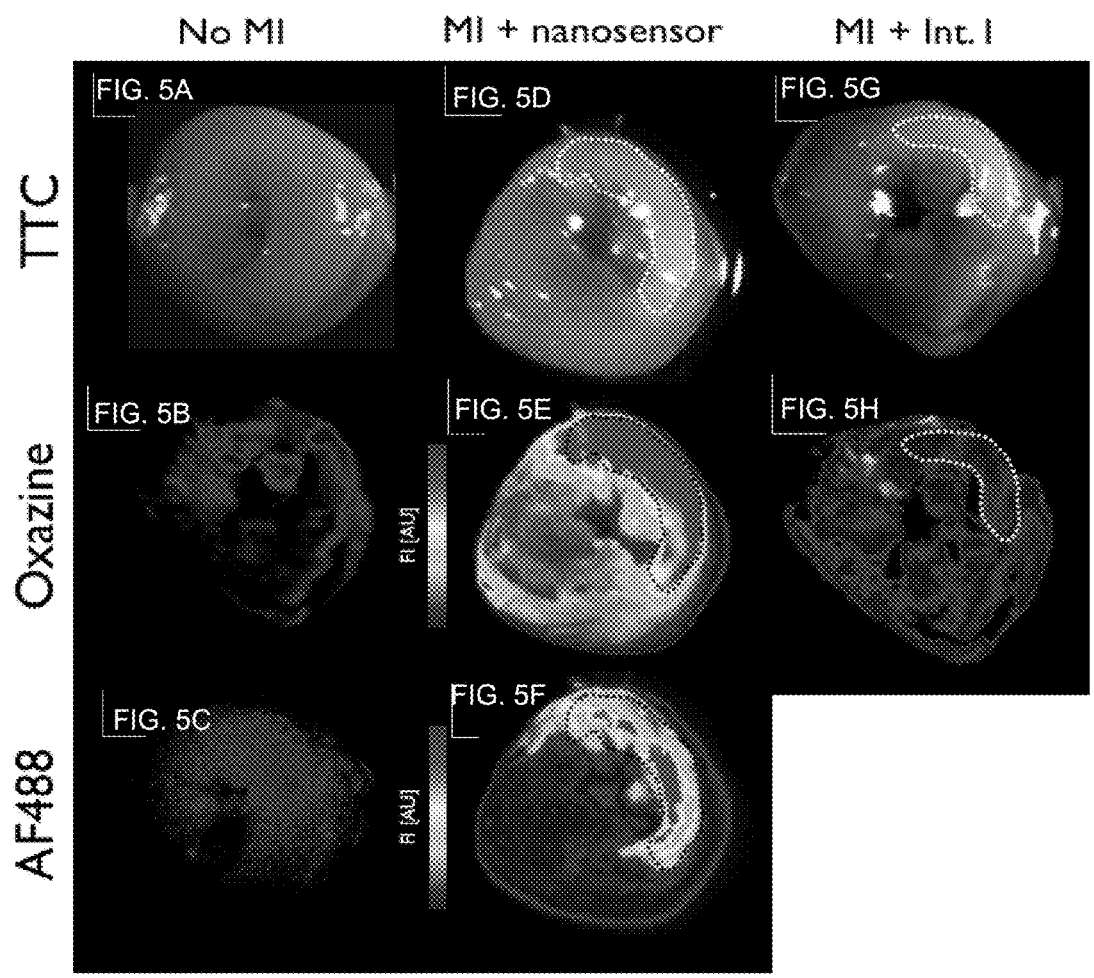

FIG. 6A
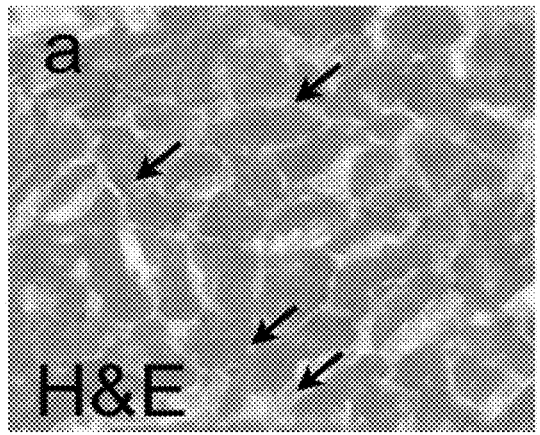
FIG. 6B
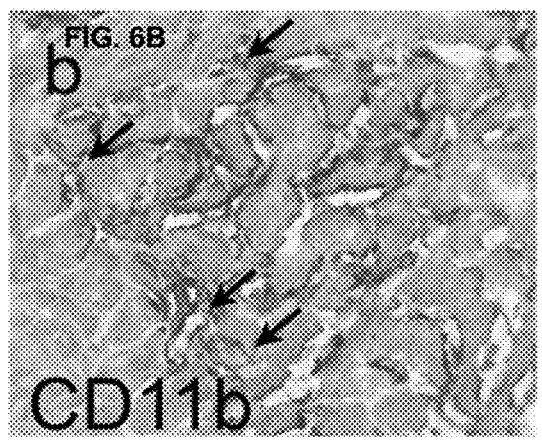
FIG. 6C
FIG. 6D
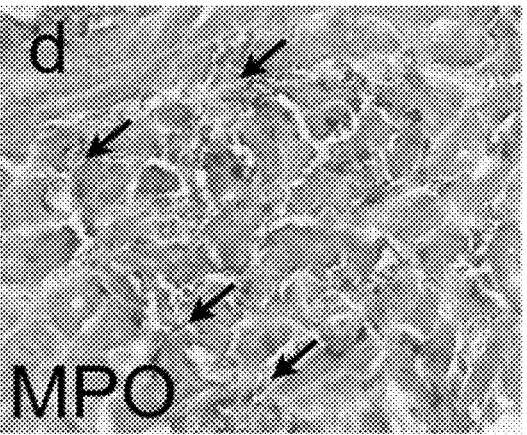
FIG. 6E
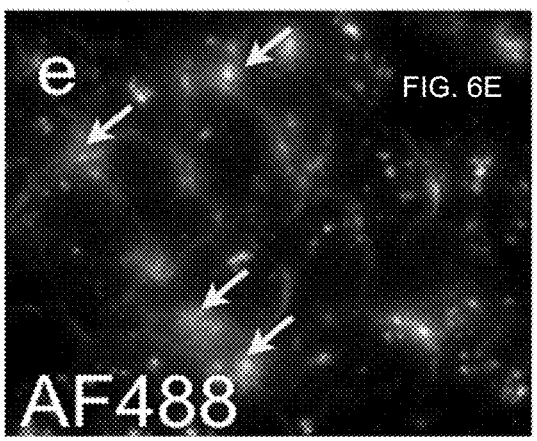
FIG. 6F
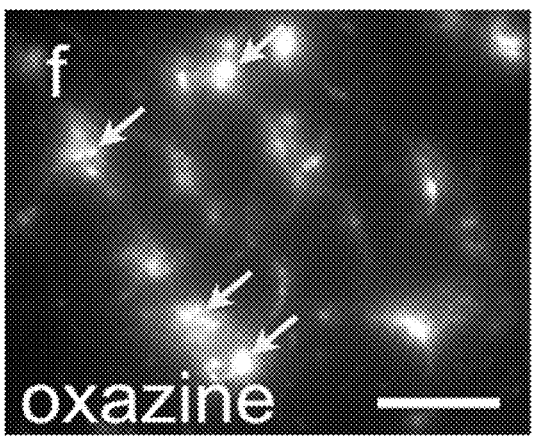

OPTICAL SENSOR CONJUGATES FOR DETECTING REACTIVE OXYGEN AND/OR REACTIVE NITROGEN SPECIES IN VIVO

CROSS REFERENCE TO RELATED APPLICATION

This application is a divisional of U.S. patent application Ser. No. 13/700,255, now issued U.S. Pat. No. 9,636,423, with a 371 filing date of Feb. 21, 2013, which is a 371 of International Application No. PCT/US2011/038903, filed Jun. 2, 2011, which claims priority from U.S. Provisional Application Ser. No. 61/350,772, filed on Jun. 2, 2010, all of which are incorporated herein by reference in their entireties.

STATEMENT REGARDING FEDERALLY SPONSORED RESEARCH OR DEVELOPMENT

The present invention was made with government support Under Grant No. 1-U01-HL080731 awarded by the National Institutes of Health. The United States Government has certain rights in the invention.

FIELD OF THE INVENTION

The present disclosure describes the design and synthesis of sensor conjugates for the detection of reactive oxygen and/or reactive nitrogen species.

BACKGROUND OF THE INVENTION

Inflammation is a ubiquitous response to acute or chronic tissue injury. Reactive oxygen and nitrogen species (ROS/RNS) generated during inflammation are causal to or can exacerbate pathogenesis of Alzheimer disease, atherosclerosis, cancer, ischemia-reperfusion injury in stroke, inflammatory bowel disease, myocardial infarction, and organ transplantation. Generation of the majority of ROS species is driven by heavy metal catalyzed oxidation reactions and enzymatically by myeloperoxidase (MPO). MPO is a heme-containing enzyme that mediates production of hypochlorious acid (HOCl/OCl$^-$) from chloride ion (Cl$^-$) and hydrogen peroxide ($H_2O_2$). MPO can accommodate and oxidize a number of small molecule substrates that bind to the active site displacing water molecules.

MPO has been shown to be a biomarker of myocardial infarction (MI) and coronary artery disease, due to the central role of MPO-dependent protein modification in the pathogenesis cardiovascular diseases. In atherosclerosis, low density lipoprotein (LDL) particles are oxidized by HOCl, chloramines, phenoxyl radical intermediates, peroxynitrite (ONOO$^-$) and MPO-dependent nitrogen dioxide ($NO_2$) production, driving lipid-laden macrophages to become atherosclerotic foam cells; the core of vulnerable plaques.

Imaging of MPO function and ROS generation in cells and animal models of human diseases has been hampered by the lack of probes with appropriate pharmacokinetics, suitable emission wavelengths to overcome tissue auto-fluorescence, and adequate specificity for relevant ROS. Tailoring of optical imaging probes for certain ROS/RNS species have been attempted with varied success for measuring nitric oxide, superoxide/OH, $H_2O_2$, ONOO$^-$, and HOCl. However, in vivo use of these probes is not practical, because most are small molecules with unfavorable washout kinetics, have poor dye properties, and/or are activated by numerous ROS. Therefore, there exists a need for new ways for monitoring ROS/RNS generation.

SUMMARY OF THE INVENTION

The present invention provides methods and compositions based on optical sensor conjugates that can be used to detect ROS/RNS, such as HOCl/OCl— and ONOO—, that are the direct result of inflammation. The optical sensor conjugates include a fluorogenic small molecule with a linker connecting the fluorogenic small molecule to a particle, e.g., nanoparticle or microparticle. The fluorogenic small molecule can be oxidized in vivo by ROS/RNS causing the small molecule to be released from the linker and fluoresce. Thus, the fluorescent small molecule can be detected, e.g., by microscopy.

Accordingly, in a first aspect the present invention provides, inter alia, methods of detecting reactive oxygen, reactive nitrogen, or both in a subject. The methods include administering to the subject an optical sensor conjugate comprising a fluorogenic small molecule, a particle or a polymer, and a linker that connects the small molecule to the particle, for a time sufficient for the small molecule to react with the reactive oxygen or reactive nitrogen, or both, thereby releasing the small molecule from the optical sensor conjugate and becoming fluorescent; and providing a fluorescence image of the subject with the small molecule, thereby imaging the subject.

In one embodiment, the small molecule with the linker is a compound of Formula I:

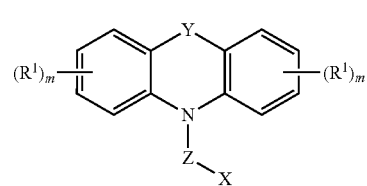

wherein:

Z is the linker and comprises $C_{3-20}$ alkyl, wherein any of the carbons in $C_{3-20}$ alkyl can be replaced with —C(O)—, C(O)O—, —C(O)NR$^A$—, —C(NH)—, oxygen, sulfur, —SO$_2$—, —NR$^A$SO$_2$——NR$^A$—;

X is selected from

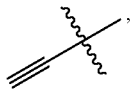

N$_3$, C(O)Cl, and C(O)OR$^A$;

Y is selected from O, S, Se, Te, N(R$^A$), and C(Me)$_2$;

R$^1$ is selected from H, $C_{1-6}$ alkyl, OR$^A$, and NR$^C$R$^D$, wherein said $C_{1-6}$ alkyl is optionally substituted by OR$^A$ or NR$^C$R$^D$;

or 2 or 3 R$^1$ adjacent to each other and together with the C atoms to which they are attached form 1 or 2 heterocycloalkyl, optionally substituted by 1, 2, 3, or 4 substituents independently selected from H, OH, $C_{1-6}$ alkyl, OR$^A$, C(O)R$^B$, C(O)NR$^C$R$^D$, and C(O)OR$^A$;

R$^A$, R$^B$, R$^C$ and R$^D$ are independently selected from H, $C_{1-6}$ alkyl, and succinimidyl; and m is 1, 2, 3, or 4.

In some embodiments, X is C(O)OR$^A$ and Y is O.

In some embodiments, R$^1$ is NR$^C$R$^D$.

In one embodiment, the invention provides a small molecule and linker, which is

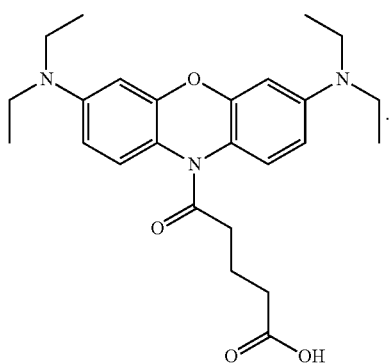 [SMILES: CCN(CC)c1ccc2c(c1)Oc1cc(N(CC)CC)ccc1N2C(=O)CCCC(=O)O]

In some embodiments, the particle further comprises a reporting agent.

In some embodiments, the fluorescence image is provided by fluorescence microscopy.

In some embodiments, the subject is a mammal.

In some embodiments, the reactive oxygen, reactive nitrogen, or both are caused by and/or associated with inflammation.

In some embodiments, the inflammation is caused by and/or associated with tissue injury.

In some embodiments, the reactive oxygen, reactive nitrogen, or both species are caused by and/or associated with Alzheimer's disease, atherosclerosis, cancer, stroke, inflammatory bowel disease, or organ transplantation.

In another aspect, the invention provides a composition for detecting reactive oxygen and reactive nitrogen species in a subject, the composition comprising: a fluorogenic small molecule, a particle, and a linker that connects the small molecule to the particle.

In some embodiments, the particle further comprises a reporting agent.

In some embodiments, the small molecule with the linker is a compound of Formula I:

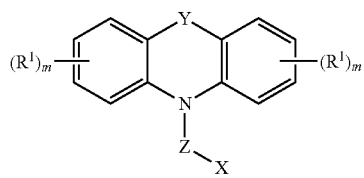

wherein:

Z is the linker and comprises $C_{3-20}$ alkyl, wherein any of the carbons in $C_{3-20}$ alkyl can be replaced with —C(O)—, C(O)O—, —C(O)NR$^A$-, —C(NH)—, oxygen, sulfur, —SO$_2$—, —NR$^A$SO$_2$— —NR$^A$—;

X is selected from

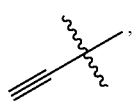 [SMILES: *C#C]

$N_3$, C(O)Cl, and C(O)OR$^A$;

Y is selected from O, S, Se, Te, N(R$^A$), and C(Me)$_2$;

R$^1$ is selected from H, $C_{1-6}$ alkyl, OR$^A$, and NR$^C$R$^D$, wherein said $C_{1-6}$ alkyl is optionally substituted by OR$^A$ or NR$^C$R$^D$;

or 2 or 3 R$^1$ adjacent to each other and together with the C atoms to which they are attached form 1 or 2 heterocycloalkyl, optionally substituted by 1, 2, 3, or 4 substituents independently selected from H, OH, $C_{1-6}$ alkyl, OR$^A$, C(O)R$^B$, C(O)NR$^C$R$^D$, and C(O)OR$^A$;

R$^A$, R$^B$, R$^C$ and R$^D$ are independently selected from H, $C_{1-6}$ alkyl, and succinimidyl; and m is 1, 2, 3, or 4.

Definitions

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms.

The term "cycloalkyl" as employed herein includes saturated cyclic, bicyclic, tricyclic, or polycyclic hydrocarbon groups having 3 to 12 carbons. Any ring atom can be substituted. The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted. The heterocyclyl groups can contain fused rings. Fused rings are rings that share a common carbon atom. Examples of heterocyclyl include, but are not limited to, piperidinyl, morpholino, pyrrolinyl, and pyrrolidinyl. The term, "compound," as used herein is meant to include all stereoisomers, geometric iosomers, tautomers, and isotopes of the structures depicted.

The term "reactive oxygen species" or "ROS" refers to reactive molecules that contain the oxygen atom. ROS are very small molecules that include oxygen ions and peroxides and can be either inorganic or organic and are highly reactive due to the presence of unpaired valence shell electrons. ROS form as a natural byproduct of the normal metabolism of oxygen and can also be generated by exogenous sources such as ionizing radiation. Examples of ROS include hydroxide radical, hypochlorite ion, hydrogen peroxide, and superoxide.

The term "reactive nitrogen species" or "RNS" refers to reactive molecules derived from nitric oxide and superoxide. Examples of RNS include peroxynitrite. Reactive nitrogen species act together with reactive oxygen species (ROS) to damage cells, causing nitrosative stress. Therefore, these two species are often collectively referred to as ROS/RNS.

By virtue of their design, the optical sensor conjugates described herein possess certain advantages and benefits. First, the optical sensor conjugates are specifically dependent on the ROS/RNS HOCl and/or ONOO—, which react with the optical sensor conjugates and cause them to release the fluorogenic small molecule from the nanoparticle. Second, the optical sensor conjugate design allows for a higher substrate target concentration with each nanoparticle delivering approximately 400 fluorogenic small molecules to the target. Third, the optical sensor conjugates demonstrate improved pharmacokinetics as compared with the free (not linked to the nanoparticle) fluorogenic small molecules.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIGS. 2A and 2B are graphs depicting spectral changes accompanying activation of an optical sensor conjugate.

FIGS. 2C and 2D are images showing the color and fluorescence changes triggered by HOCl oxidation and release of the fluorescent small molecule.

FIGS. 5A-H are images of an ex vivo comparison of an optical sensor conjugate or a representative fluorogenic small molecule with the attached linker injected into mouse tissue and the fluorescence signal associated with a representative oxidized oxazine release, accumulation, and probe washout kinetics.

FIGS. 6A-F are images of in vivo uptake and activation of an MPO optical sensor conjugate applied to infarcted heart tissue.

DETAILED DESCRIPTION OF THE INVENTION

Figure 1A:
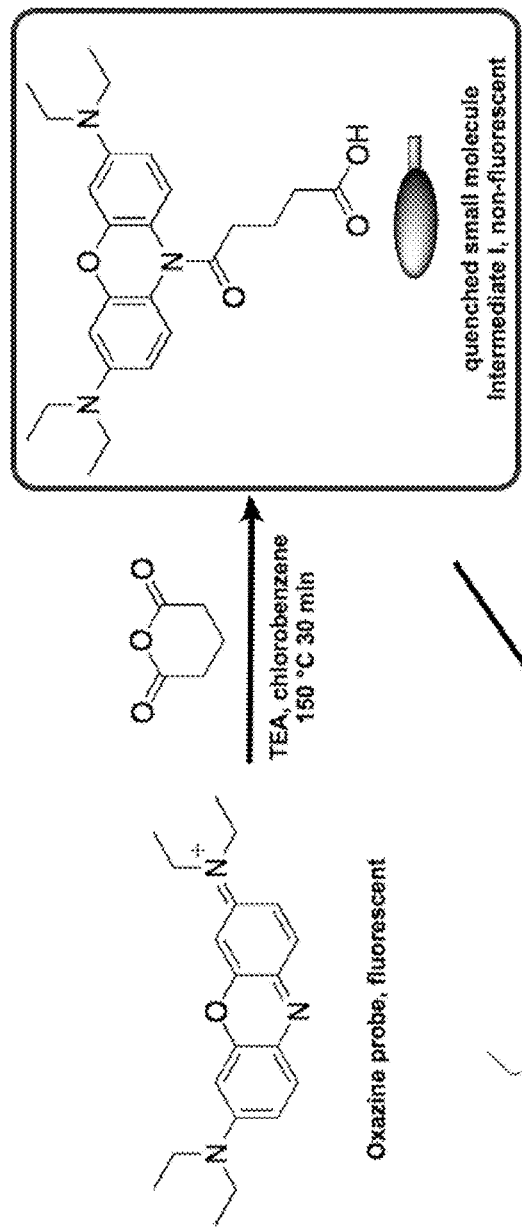
FIGS. 1A and 1B are schematics of the synthesis of an exemplary optical sensor conjugate.
Figure 1B:
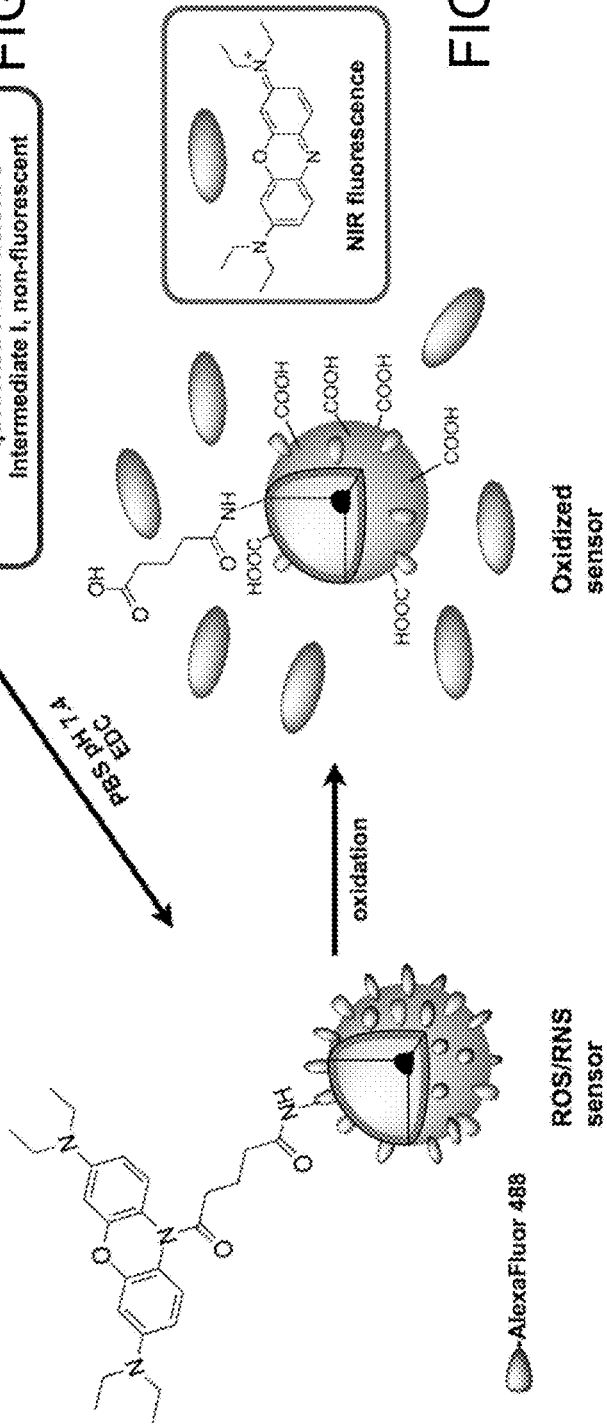
Figure 1C:
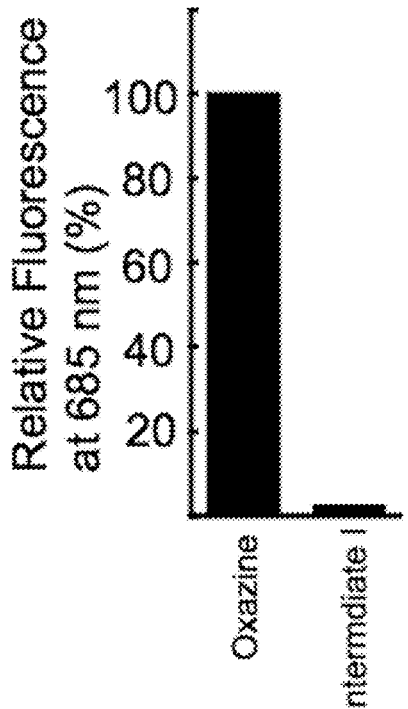
FIGS. 1C and 1D are bar graphs depicting the relative fluorescence signals for a representative fluorescent small molecule and a non-fluorescent small molecule with linker.
Figure 1E:
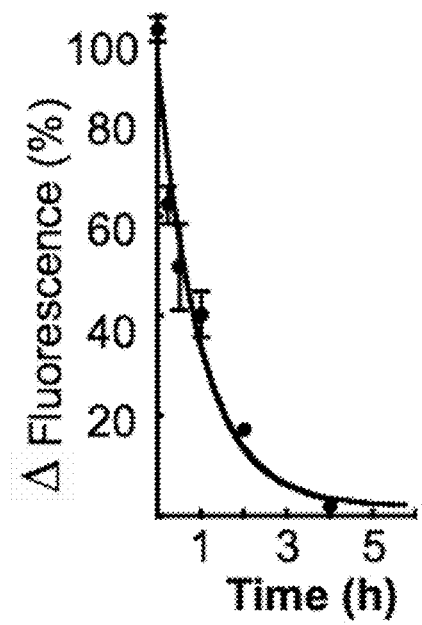
FIGS. 1E and 1F are graphs depicting the change in fluorescence signal for the determination of blood half-life for a free small molecule with a linker and an optical sensor conjugate.
Figure 1D:
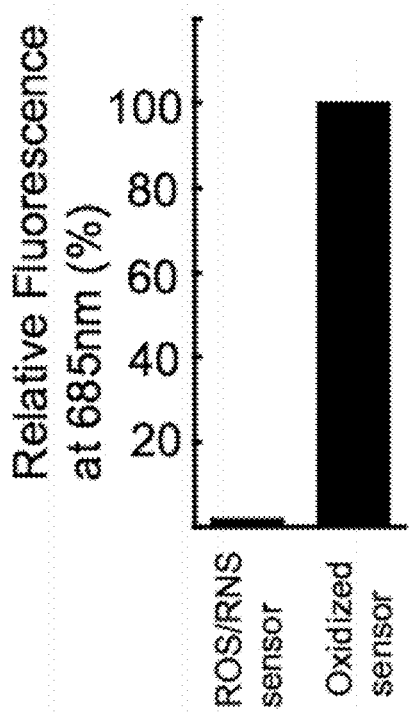
Figure 1F:
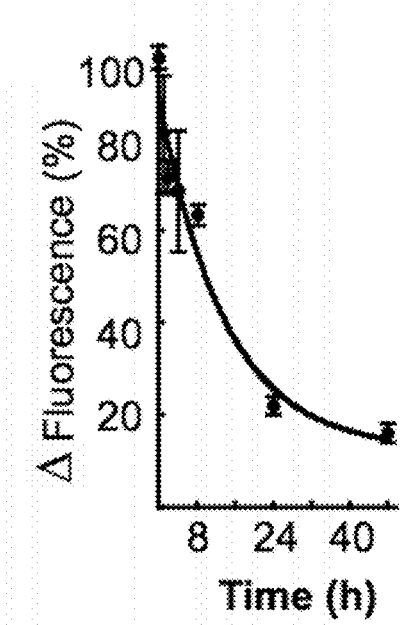

The present invention provides methods and compositions for detecting ROS/RNS in vivo that are the direct result of inflammation. These methods include the use of an optical sensor conjugate that includes a fluorogenic small molecule, a nanoparticle, and a linker connecting the fluorogenic small molecule to the nanoparticle (Scheme 1). The fluorogenic small molecule can be oxidized in vivo by ROS/RNS causing the small molecule to be released from the conjugatable linker and become fluorescent. Thereafter, the fluorescent small molecule can be detected in vivo by various techniques and systems including flow cytometry, fluorescence reflectance imaging (FRI), fluorescence molecular tomography (FMT), and microscopic fluorescence imaging.

Scheme 1

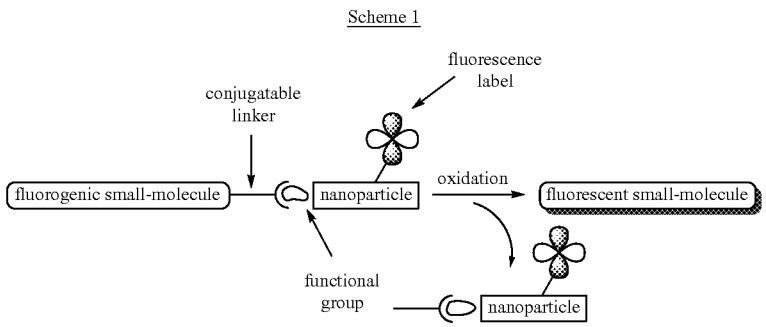

Structure of Optical Sensor Conjugates

The optical sensor conjugates are comprised of a fluorogenic small molecule, a nanoparticle, and a linker connecting the fluorogenic small molecule to the nanoparticle.

Fluorogenic Small Molecule

The fluorogenic small molecule can be any low molecular weight organic compound, i.e., less than about 2000 Daltons, that is "masked" as a non-fluorescent molecule when attached to the linker, but upon reaction with ROS/RNS, are oxidized and released from the linker as a fluorescent small molecule. One such example is an oxazine, e.g., phenoxazine or phenothiazine, which can be oxidized in vivo by either reactive oxygen or reactive nitrogen species, or both, and as a result of the oxidation become a fluorescent small molecule. The fluorogenic small molecule can also contain additional heterocyclic rings, such as but not limited to, piperidine, fused to the phenyl group of the phenoxazine or phenothiazine, carbazine, nile blue, or nile red based fluorophore.

Linker

The term "linker" as used herein refers to a group of atoms, e.g. 3-100 atoms, and may be comprised of the atoms or groups, but not limited to, carbon, amino, alkylamino, oxygen, sulfur, sulfoxide, sulfonyl, carbonyl, and imine. The linker is connected to the fluorogenic small molecule through an amide bond at a first end of the linker. In addition, the linker is connected at a second end to the nanoparticle through a covalent bond to a functional group on the nanoparticle. The covalent bond is, but is not in any way limited to, an amide bond, an ester bond, an ether or amino bond linkage, a triazole moiety synthesized through the reaction of a terminal alkyne and an azide via "click chemistry".

Various methods are known to attach the linker at the first end to a small molecule using covalent bonds. Similar methods can also be employed to attach the linker at the second end to the nanoparticle. In one example, the linker can be attached to the fluorogenic small molecule by forming an amide bond between a carboxyl (or maleimide) on the linker and the amine located on the fluorogenic small molecule. In the same way, the second end of the linker can be attached to the nanoparticle by forming an amide bond between a carboxyl (or maleimide) on the linker and an amine located on the nanoparticle. Reagents that can be used include EDC/NHS or SPDP (N-Succinimidyl 3-[2-pyridyldithio]-propionate) in both aqueous and organic solvents (such as, but not limited to, dichloromethane, acetonitrile, chloroform, tetrahydrofuran, acetone, formamide, dimethylformamide, pyridine, dioxane, or dimethysulfoxide).

In addition, various methods are known to attach the linker to the nanoparticle. For example, "click chemistry" can be used to attach the linker to the nanoparticle (see, e.g., the Sigma Aldrich catalog and U.S. Pat. No. 7,375,234, which are both incorporated herein by reference in their entireties). Of the reactions comprising "click" chemistry, one example is the Huisgen 1,3-dipolar cycloaddition of alkynes to azides to form 1,4-disubstituted-1,2,3-triazoles. The copper (I)-catalyzed reaction is mild and very efficient, requiring no protecting groups, and requiring no purification in many cases. The azide and alkyne functional groups are generally inert to biological molecules and aqueous environments.

The linker may also comprise part of a saturated, unsaturated, or aromatic ring, including polycyclic and heteroaromatic rings wherein the heteroaromatic ring is an aryl group containing from one to four heteroatoms, N, O, or S. Specific examples include, but are not limited to, unsaturated alkanes, polyethylene glycols, and dextran polymers.

In addition, the linker must meet the following two criteria. First, the linker must not interfere with the oxidation of the fluorogenic small molecule. Second, the linker can be cleaved from the fluorogenic small molecule upon oxidation of the fluorogenic small molecule.

Particle

The optical sensor conjugates include a particle or alternatively a polymer that forms the core of the conjugates. These particles can be nanoparticles or microparticles. The term "nanoparticle" refers to a particle that has a characteristic dimension of less than about 1 micrometer, where the characteristic dimension is the largest cross-sectional dimension of a particle. For example, the particle may have a characteristic dimension of less than about 500 nm, less than about 250 nm, less than about 150 nm, less than about 100 nm, less than about 50 nm, less than about 30 nm, less than about 10 nm, or less than about 3 nm in some cases. Microparticles with a size of between 1.0 and 100 μm can also be employed in the new conjugates. The polymer can have a molecular weight from 2 to 2,000 Kilodaltons.

The particles or polymers useful in the methods and compositions described herein are made of materials that are (i) biocompatible, i.e., do not cause a significant adverse reaction in a living animal when used in pharmaceutically relevant amounts; (ii) feature functional groups to which the fluorogenic small molecule can be covalently attached; (iii) exhibit low non-specific binding of interactive moieties to the particles; and (iv) are stable in solution, i.e., the particles or polymers do not precipitate. Optionally, the particles or polymers can include a reporting agent, such as a fluorescent dye. The particles or polymers can be monodisperse (a single crystal of a material, e.g., a metal, per particle, or have a discrete molecular weight) or polydisperse (particles with range of different diameters, or polymers with a range of molecular weights).

A number of particles are known in the art, e.g., organic or inorganic nanoparticles. Liposomes, dendrimers, carbon nanomaterials and polymeric micelles are examples of organic nanoparticles. Inorganic particles include metallic particles, e.g., Au, Ni, Pt and $TiO_2$ particles. For example, magnetic nanoparticles can also be used, e.g., spherical nanocrystals of 10-20 nm with a $Fe^{2+}$ and/or $Fe^{3+}$ core surrounded by dextran or PEG molecules. In some embodiments, colloidal gold nanoparticles are used, e.g., as described in Qian et al., Nat. Biotechnol. 26: 83-90 (2008); U.S. Pat. Nos. 7,060,121; 7,232,474; and U.S. P.G. Pub. No. 2008/0166706. Suitable multifunctional nanoparticles, and methods for constructing and using multifunctional nanoparticles, are discussed in e.g., Sanvicens and Marco, Trends Biotech., 26:425-433 (2008). A number of different polymers are known in the art. These can include, but are not limited to dextrans, aminodextrans, carboxymethyldextrans, carboxymethylstarches, polyvinyl alcohols, polyethylene glycols, poly-lysines, or poly-glutamic acids.

The particles or polymers are attached to the linker and thus to the fluorogenic small molecules described herein via a functional group. In some embodiments, the particles are associated with a polymer that includes the functional groups, and also serve to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, aminodextran, carboxmethyl dextran, and/or reduced carboxymethyl dextran. The metal oxide can be a collection of one or more crystals that contact each other, or that are individually entrapped or surrounded by the polymer.

In some embodiments, the particles are associated with non-polymeric functional group compositions. Methods are known to synthesize stabilized, functionalized particles without associated polymers, which are also within the scope of this invention. Such methods for use to make nanoparticles are described, for example, in Halbreich et al., *Biochimie,* 80:379-90, 1998.

In some embodiments, the nanoparticles have an overall size of less than about 1-100 nm, e.g., about 25-75 nm, e.g., about 40-60 nm, or about 50-60 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 60 nm.

In some embodiments, the fluorogenic small molecule can be conjugated to polymers. For example the fluorogenic small molecule can be conjugated to poly-lysine or amino dextran, or to larger polymers which can provide the same benefits that the nanoparticles do with regard to in vivo pharmacokinetics In some embodiments, the nanoparticle has a reporter group, such as a fluorescent dye attached, e.g., to the functional groups. In one example, the nanoparticle can be fluorescence labeled with Alexa Fluor® 488 which has an absorption maximum of about 496 nm and an emission maximum of 519 nm (green color). It is important that the absorption and emission of the fluorescently labeled nanoparticles not interfere with the imaging of the fluorescent small molecule.

Synthesis of Particles

There are varieties of ways that the particles can be prepared, but in all methods, the result must be a particle with functional groups that can be used to link the nanoparticle to the fluorogenic small molecule.

In all embodiments, the fluorogenic small molecule is attached to the particle via a linker. The linker is attached to the fluorogenic small molecule at a first end and to a functional group on the particle at the second end of the linker. There are several methods for placing a functional group, such as a carboxy or amino, on the particle. Methods for synthesizing functionalized, coated particles are discussed in further detail below.

Carboxy functionalized nanoparticles can be made, for example, according to the method of Gorman (see WO 00/61191). Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can also be made and crosslinked, e.g., with epichlorohydrin. The addition of ammonia will react with epoxy groups to generate amine groups, see Hogemann et al., *Bioconjug. Chem.* 11:941-6 (2000), and Josephson et al., *Bioconjug. Chem.*, 10:186-91 (1999).

Carboxy-functionalized nanoparticles can be converted to amino-functionalized magnetic particles by the use of water-soluble carbodiimides and diamines such as ethylene diamine or hexane diamine.

Methods of Detecting Optical Sensors

The compounds and compositions described herein can be used in in vivo imaging methods known in the art, e.g., as described in US 2005/0249668. General principles of fluorescence, optical image acquisition, and image processing can be applied in the practice of the invention. For a review of optical imaging techniques, see, e.g., Alfano et al., *Ann. NY Acad. Sci.*, 820:248-270, 1997. Imaging systems typically include three basic components: (1) a near infrared light source, (2) an apparatus for separating or distinguishing emissions from light used for chromophore excitation, and (3) a detection system.

For example, the light source can provide monochromatic (or substantially monochromatic) near infrared light. The light source can be a suitably filtered white light, e.g., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; Alexander, *J. Clin. Laser Med. Surg.* 9:416-418, 1991. Information on near infrared lasers for imaging can also be found on the Internet (e.g., at imds.com) and various other well-known sources.

A high pass or bandpass filter (e.g., 655 nm) can be used to separate optical emissions from excitation light. Suitable high pass or bandpass filters are commercially available from Omega Optical. In some embodiments, a single excitation wavelength can be used to excite multiple different fluorochromes on a single probe or multiple probes (with different activation sites), and spectral separation with a series of bandpass filters, diffraction grating, or other means can be used to independently read the different activations.

In general, the light detection system can include light-gathering/image-forming and light-detection/image-recording components. Although the light-detection system can be a single integrated device that incorporates both components, the light-gathering/image-forming and light-detection/image-recording components will be discussed separately. However, a recording device may simply record a single (time varying) scalar intensity instead of an image. For example, a catheter-based recording device can record information from multiple sites simultaneously (i.e., an image), or can report a scalar signal intensity that is correlated with location by other means (such as a radio-opaque marker at the catheter tip, viewed by fluoroscopy).

A particularly useful light-gathering/image-forming component is an endoscope. Endoscopic devices and techniques that have been used for in vivo optical imaging of numerous tissues and organs, including peritoneum (Gahlen et al., *J. Photochem. Photobiol. B* 52:131-135, (1999)), ovarian cancer (Major et al., *Gynecol. Oncol.* 66:122-132, (1997)), colon (Mycek et al., *Gastrointest. Endosc.* 48:390-394, 1998; Stepp et al., *Endoscopy* 30:379-386, (1998)) bile ducts (Izuishi et al., *Hepatogastroenterology* 46:804-807, (1999)), stomach (Abe et al., *Endoscopy* 32:281-286, (2000)), bladder (Kriemair et al., *Urol. Int.* 63:27-31, (1999); Riedl et al., *J. Endourol.* 13:755-759, (1999)), and brain (Ward, *J. Laser Appl.* 10:224-228, (1998)), can be employed in the practice of the present invention. Other types of light gathering components useful in the methods described herein are catheter-based devices, including fiber optic devices. Such devices are particularly suitable for intravascular imaging. See, e.g., Tearney et al., *Science* 276:2037-2039, (1997); Boppart et al., *Proc. Natl. Acad. Sci. USA* 94:4256-4261, (1997).

Still other imaging technologies, including phased array technology (Boas et al., *Proc. Natl. Acad. Sci. USA* 91:48874891, (1994); Chance, *Ann. NY Acad. Sci.* 838:29-45, (1998)), diffuse optical tomography (Cheng et al., *Optics Express* 3:118-123, (1998); Siegel et al., *Optics Express* 4:287-298, (1999)), intravital microscopy (Dellian et al., *Br. J. Cancer* 82:1513-1518, (2000); Monsky et al, *Cancer Res.* 59:4129-4135, (1999); Fukumura et al., *Cell* 94:715-725, (1998), fluorescence molecular tomography (FMT), fluorescence reflectance imaging (FRI), and confocal imaging (Korlach et al., *Proc. Natl. Acad. Sci. USA* 96:8461-8466, (1999); Rajadhyaksha et al., *J. Invest. Dermatol.* 104:946-

952, (1995); Gonzalez et al., *J. Med.* 30:337-356, (1999)) can be employed in the practice of the present methods.

Any suitable light-detection/image-recording component, e.g., charge-coupled device (CCD) systems or photographic film, can be used. The choice of light-detection/image-recording component will depend on factors including type of light gathering/image forming component being used. Selecting suitable components, assembling them into a near infrared imaging system, and operating the system is within the ability of a person of ordinary skill in the art.

In addition, the compositions and methods of the present invention can be used in combination with other imaging compositions and methods. For example, the agents of the present invention can be imaged by NIR imaging methods either alone or in combination with other traditional imaging modalities, such as, X-ray, computed tomography (CT), MR imaging, ultrasound, positron emission tomography (PET), and single photon computerized tomography (SPECT). For instance, the methods described herein can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents.

Uses of Optical Sensor Conjugates

The compounds and compositions described herein are optical sensor conjugates that include a fluorogenic small molecule, an optionally fluorescent labeled nanoparticle or polymer, and a linker connecting the fluorogenic small molecule to the optionally fluorescence labeled nanoparticle. The optical sensor conjugates are useful for detecting and/or monitoring reactive oxygen and/or reactive nitrogen species, which include peroxynitrite (ONOO—) and myeloperoxidase (MPO) mediated hypochlorous acid (HOCL/OCl—) production. The optical sensor conjugates are, however, stable toward oxidants such as hydroxyl radical, hydrogen peroxide, and superoxide. The reactive oxygen and reactive nitrogen species oxidize the fluorogenic small molecule to release the small molecule from the linker and become fluorescent. As a result, the fluorescent small molecule can be detected using flow cytometry, fluorescence reflectance imaging, and microscopic fluorescence imaging.

In Vivo Imaging

The compounds and compositions can be used in in vivo imaging methods. In general, such methods include administering to a subject one or more optical sensor conjugates described herein; optionally allowing the optical sensor conjugates to distribute within the subject; exposing the subject to light of a wavelength absorbable by at least one fluorophore in the imaging agent; and detecting an optical signal emitted by the fluorophore. The emitted optical signal can be used to construct an image. The image can be a tomographic image. Furthermore, it is understood that the methods (or portions thereof) can be repeated at intervals to evaluate the subject over time.

The illuminating and/or detecting steps can be performed using any device or apparatus known in the art, e.g., an endoscope, catheter, tomographic system, planar system, hand-held imaging system, or an intraoperative imaging system or microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as combined images.

Information provided by such in vivo imaging, for example, the presence, absence, or level of emitted signal, can be used to detect and/or monitor tissue damage, inflammation, and/or disease in the subject. Examples of causes of tissue damage include, without limitation, Alzheimer's disease, atherosclerosis, cancer, stroke, inflammatory bowel disease, and organ transplant. In addition, in vivo imaging can be used to assess the effect of a compound or therapy by using the optical sensor conjugate, wherein the subject is imaged prior to and after treatment with the compound or therapy, and the corresponding signal/images are compared.

The methods and compositions described herein can be used to help a physician or surgeon to identify and characterize areas of disease, such as cancers and atherosclerosis, and to distinguish between dead or dying tissue after suffering a heart attack or stroke.

The methods and compositions described herein can also be used in the detection, characterization, and/or determination of the localization of a disease, especially early disease, the severity of a disease or a disease-associated condition, the staging of a disease, and/or monitoring a disease. The presence, absence, or level of an emitted signal can be indicative of a disease state.

The methods and compositions disclosed herein can also be used to monitor and/or guide various therapeutic interventions, such as surgical procedures, and monitoring drug therapy, including cell based therapies. The methods can also be used in prognosis of a disease or disease condition.

With respect to each of the foregoing, examples of such disease or disease conditions that can be detected and/or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, hypertension, stroke, myocardial infarction, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein, therefore, can be used, for example, to determine the presence and/or localization of tumor cells, the presence and/or localization of inflammation, including the presence of activated macrophages, for instance in atherosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compositions described herein, can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to the imaging agents.

Compositions

The optical sensor conjugates described herein can be provided dry or dissolved in a carrier or vehicle, e.g., pharmaceutically acceptable carriers and vehicles. Useful carriers and vehicles include, but are not limited to, buffer substances such as phosphate, glycine, sorbic acid, potassium sorbate, tris(hydroxymethyl)amino methane ("TRIS"), partial glyceride mixtures of fatty acids, water, salts or electrolytes, disodium hydrogen phosphate, potassium hydrogen phosphate, and sodium chloride.

The optical sensor conjugates can be administered in the form of a sterile injectable preparation. The possible vehicles or solvents that can be used to make injectable preparations include water, Ringer's solution, and isotonic sodium chloride solution, and 5% D-glucose solution (D5W). In addition, oils such as mono- or di-glycerides and fatty acids such as oleic acid and its derivatives can be used. The compounds and compositions can be administered orally, parenterally, by inhalation, topically, rectally, nasally, buccally, vaginally, or via an implanted reservoir. The term "parenteral administration" includes intravenous, intramuscular, intra-articular, intrasynovial, intrasternal, intrathecal, intraperitoneal, intracisternal, intrahepatic, intralesional, and intracranial injection or infusion techniques. The optical sensor conjugates can also be administered via catheters or through a needle to any tissue.

Dosing of the optical sensor conjugate will depend on a number of factors including the sensitivity of the detection system used, as well as a number of subject-related variables, including animal species, age, body weight, mode of administration, sex, diet, time of administration, and rate of excretion.

Prior to use of the invention or any pharmaceutical composition of the invention, the subject can be treated with an agent or regimen to enhance the imaging process. For example, a subject can be put on a special diet prior to imaging to reduce any auto-fluorescence or interference from ingested food, such as a low pheophorbide diet to reduce interference from fluorescent pheophorbides that are derived from some foods, such as green vegetables. Alternatively, a cleansing regimen can be used prior to imaging, such as those cleansing regimens that are used prior to colonoscopies and include use of agents such as Visiciol™. The subject (patient or animal) can also be treated with pharmacological modifiers to improve image quality. For example, using low dose enzymatic inhibitors to decrease background signal relative to target signal (secondary to proportionally lowering enzymatic activity of already low-enzymatic activity normal tissues to a greater extent than enzymatically-active pathological tissues) can improve the target-to-background ratio during disease screening.

EXAMPLES

The invention is further described in the following examples, which do not limit the scope of the invention described in the claims.

Example 1.

Synthesis of an Optical Sensor Conjugate Employing an Oxazine

Oxazine, as its perchlorate salt, was purchased from Acros Organics USA (Morris Plains, N.J.) and used as received. Alexafluor® 488 (AF488) succinimidyl ester was purchased from Molecular Probes. All other chemicals and solvents, unless noted, were purchased from Sigma-Aldrich or Fisher Scientific. Preparative high performance liquid chromatography (HPLC) was performed on a Varian 210 instrument equipped with a 335 diode array detector and a Varian Pursuit XRs 10 C18 250×21.2 mm column at a flow rate of 20 mL/min. All $^1$H (400 MHz) and $^{13}$C NMR (100 MHz) nuclear magnetic resonance (NMR) spectra were acquired on a Bruker DPX-400 spectrometer at ambient temperature and were referenced to tetramethylsilane as an internal standard. Absorption spectra were collected on a Varian Cary 50-Bio UV/visible spectrophotometer.

For determination of the extinction coefficient of the fluorescent small molecule, fresh stock solutions of the fluorescent small molecule were prepared for each trial by dissolution of 2-4 mg portions of the dye, weighed on a Mettler AT201 analytical balance with an error of ±0.01 mg, in PBS, pH 7.4, using a 10 mL volumetric flask. Standard deviations for the extinction coefficient measurements, performed in triplicate, were 5% or less. Fluorescence data were collected on a Varian Cary Eclipse fluorescence spectrophotometer. High-resolution electrospray ionization (ESI) mass spectra were collected on a Bruker Daltonics APEXII 3 T Fourier transform mass spectrometer in the Department of Chemistry Instrumentation Facility at the Massachusetts Institute of Technology.

Synthesis of sodium 5-(3,7-bis(diethylamino)-10H-phenoxazin-10-yl)-5-oxopentanoate (intermediate 1)

To oxazine perchlorate (1) (42.4 mg, 0.1 mmol) and glutaric anhydride (114 mg, 1 mmol) in chlorobenzene (0.5 mL) was added triethylamine (279 µL, 2 mmol). The dark blue mixture was heated in a sealed thick-walled pressure tube at 150° C. for 30 min. After cooling the now brown reaction mixture was concentrated by rotary evaporation and the crude product was re-dissolved in DMF (2 mL).

Preparative HPLC of the crude reaction using a gradient from 0 to 50% buffer B over 30 min afforded the purified intermediate as its free acid. Buffer A consists of water with 0.1% trifluoroacetic acid (TFA) and buffer B is acetonitrile with 10% water and 0.1% TFA. The product was concentrated to ~5 mL by rotary evaporation. When dried, the free acid of the intermediate is very hygroscopic. To this hygroscopic form, the 5 mL acidic solution containing the free acid was neutralized with 0.1 M bicarbonate buffer, pH 7.4. After neutralization, the cloudy suspension was loaded onto a 10 g reverse phase C18 silica-desalting column (Waters Corp.). The excess inorganic salts were removed by washing with 50 mL of deionized water, and pure intermediate 1 (30.0 mg, 65%) as its sodium salt was isolated by elution with a mixture of acetonitrile containing 25% water. The purity of the product was verified to be >97% by analytical HPLC.

$^1$H NMR (400 MHz, CD$_3$OD): δ 7.24 (d, 2H, J=8.4 Hz), 6.42-6.38 (m, 4H), 3.32 (quartet, 8H, J=7.1 Hz), 2.63 (t, 2H, J=7.5 Hz), 2.17 (t, 2H, J=7.5 Hz), 1.88 (pentet, 2H, J=7.4 Hz), 1.11 (t, 12H, J=7.0 Hz). $^{13}$C NMR (400 MHz, CD$_3$OD): δ 181.8, 175.3, 154.6, 149.2, 127.4, 120.1, 108.4, 101.5, 46.4, 35.5, 34.5, 24.1, 13.7. HRMS-ESI [M-H]$^-$ m/z calcd. for [C$_{25}$H$_{32}$N$_3$O$_4$]$^-$ 438.2398, found 428.2398.

Synthesis of the ROS/RNS nanoparticle conjugate

Alexa Fluor 488 labeled CLIO nanoparticles (hydrodynamic diameter 41 nm as determined by dynamic light scattering) were prepared according to published procedures (Koch et al. *Bioconjug Chem* 14, 1115-21, (2003). To a solution of CLIO-AF488 (3 mg Fe) in 2.7 mL of PBS, pH 7.4 was added intermediate 1 (3 mg, 6.5 μmol) dissolved in 300 μL of DMSO and N-(3-Dimethylaminopropyl)-N'-ethylcarbodiimide hydrochloride (EDAC, 30 mg, 0.16 mmol). This solution was allowed to stir in overnight (dark, room temperature). Following incubation, the labeled conjugate was purified by size exclusion chromatography (Sephadex G-50 resin) eluting with PBS, pH 7.4. The purified nanoparticle solution was concentrated to 1 mL by centrifugal filtration with an Amicon Ultra 3,000 MW cutoff centrifugal filter. The concentration of this stock solution (2.25 mg Fe/mL) was determined by comparing the absorbance at 400 nm (a wavelength at which AF488 and intermediate 1 do not absorb) to a diluted CLIO-AF488 stock solution of known concentration.

The number of fluorogenic small molecules with linker per nanoparticle, which have no absorption in the visible spectrum, was determined by activation of a dilute 10 nM solution of the final optical sensor conjugate with excess NaOCl or peroxynitrite. The concentration of the released oxazine fluorophore was then measured using its extinction coefficient in PBS (ε=107,000 M-1 cm-1). Using this procedure, the number of ROS activatable oxazine groups per nanoparticle is calculated to be ~400.

The optical sensor conjugate was synthesized by the reaction scheme in FIG. 1$a$-$b$ and is based on the HOCl/ONOO$^-$ dependent release of the small molecule from the parent nanoparticle. The linker was engineered to be attached to the small molecule (FIG. 1$a$) that is non-fluorescent (FIG. 1$c$), which was used for attachment to the Alexa Flour 488-modified magnetic nanoparticle (FIG. 1$b$). The nanoparticle by itself (without a small molecule) has been studied extensively (Josephson et al. *Bioconjug Chem*, 10:186-91 (1999)) and has been used in humans (Harisinghani, et al. *Neoplasia*, 9:1160-5 (2007)). This sensor design results in a high substrate target concentration with each nanoparticle containing ~400 activatable oxazine functionalities. Activation of the optical sensor conjugate by HOCl generated from the MPO/H$_2$O$_2$/Cl$^-$ system results in release of the fluorescent small molecule from the nanoparticle scaffold and restoration of its fluorescent properties (FIG. 1$d$), while retaining the covalent Alexa Fluor 488 labels (FIG. 1$b$).

Example 2

Optical Sensor Conjugate Blood Half-life

In vivo pharmacokinetics of the small molecule alone and the optical sensor conjugate were determined in groups of mice. Each group consisted of 5 mice (C57/B6, Jackson Labs) that were injected either with the small molecule, oxazine (50 nmol), or the nanoparticle, optical sensor conjugate (8-10 mg/kg body weight) while anesthetized (isoflurane 2-3% v/v+2 L/min O$_2$). Retro-orbital bleeds were taken at various times and immediately transferred to a tube containing anticoagulant heparin. The blood samples were then imaged on the Bonsai fluorescence reflectance imaging system (Siemens) using the Cy 5 channel (l$_{exc}$=620-650 nm with l$_{em}$ 680-710 nm) for oxazine and GFP channel (l$_{exc}$=450-480 nm with l$_{em}$ 500-530 nm) for the AF488-labeled optical sensor conjugate due to the quenched nature of the fluorogenic small molecule attached to the nanoparticles. Fluorescence measurements were corrected for control background levels (blood from un-injected control mice) and expressed as percent injected dose.

The attachment of the small molecule to the nanoparticle significantly increases the blood half-life of the circulating conjugate from ~40 minutes to over 9 hours (FIGS. 1$e$-$f$), as compared to the free small molecule, making it suitable for animal imaging. The oxidation of the sensor causes absorbance spectral changes as shown in FIG. 2$a$, marked by the generation the free oxazine with l$_{max}$ of 655 nm (c=107,000 M$^{-1}$ cm$^{-1}$) and a dramatic reaction color change from orange to green (FIG. 2$c$). Activation of the optical sensor conjugate and release of the fluorescent small molecule after exposure to excess NaOCl generates a >500-fold increase in fluorescence emission at l$_{max}$ of 672 nm (l$_{exc}$=620 nm, FIG. 2$b$) and release of the fluorescent dye (FIG. 2$d$).

Figure 3A:
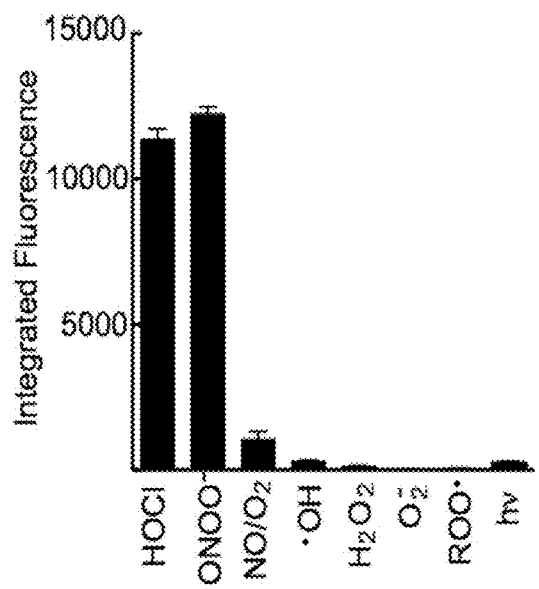
FIG. 3A is a bar graph depicting the fluorescence response of an optical sensor conjugate following incubation with a panel of biologically relevant oxidants.
Figure 3B:
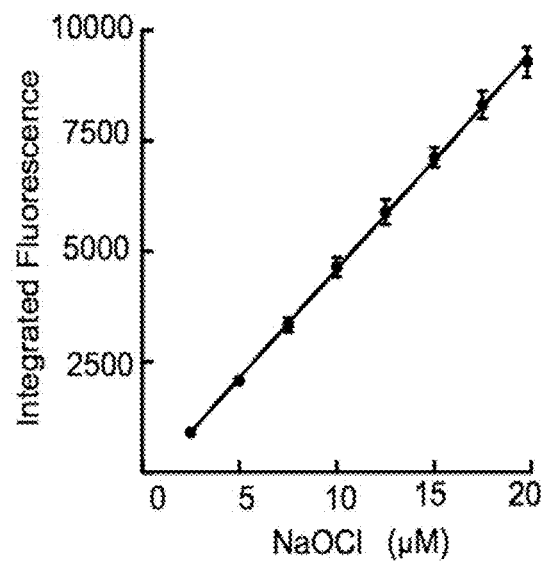
FIG. 3B is a line graph depicting the dependence of a representative oxazine on increasing HOCl concentration.
Figure 3C:
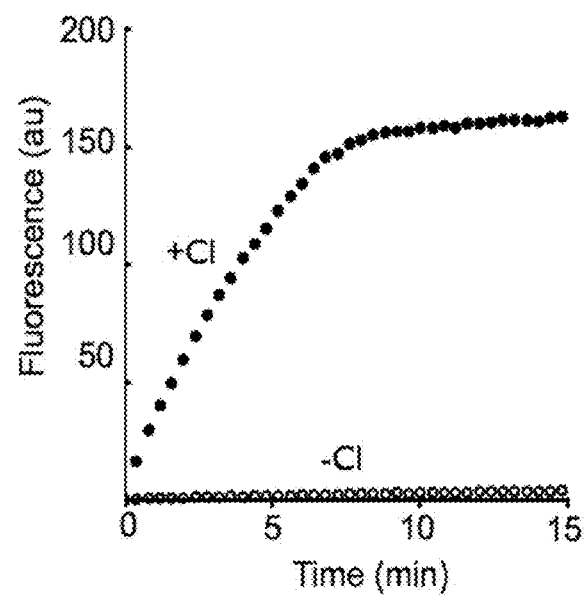
FIG. 3C is a line graph showing the effect of chloride ions on activation of an optical sensor conjugate and release of an oxidized oxazine.

The specificity of the optical sensor conjugate towards activation by a panel of ROS species was determined, with only HOCl and ONOO$^-$ able to cause oxazine release (FIG. 3$a$). Importantly, no activation was observed by H$_2$O$_2$, OH., NO/O$_2$, and O$_2$·. Both HOCl/OCl$^-$ and ONOO$^-$ are known to be induced in ischemia/reperfusion injury (Yasmin et al. *Cardiovasc Res* 33:422-32 (1997)). The optical sensor conjugate activation is linear over a μM concentration range of NaOCl (FIG. 3$b$). The rate of HOCl production by stimulated neutrophils is ~0.1 fM HOCl/sec (Aratani et al. *Infect Immun* 67:1828-36 (1999)), assuming 10$^6$ neutrophils in a mouse infarct this would represent 0.1 nM HOCl/sec. The actual concentration of HOCl produced by myeloid cells in vivo in response to injury is unclear due to confounding factors such as in vivo cellular half-life of the ROS species, variability of tissue response to ischemic trauma, and rate of extracellular HOCl diffusion. Progress curves for MPO-dependent activation of the optical sensor conjugate in the presence and absence of Cl$^-$ ions indicate activation of the optical sensor conjugate is stringently dependent on the formation of HOCl and not simply on the content of OH. radicals or H$_2$O$_2$ (FIG. 3$c$).

Example 3

Selectivity of the Optical Sensor Conjugate for ROS Species

All in vitro activation experiments were performed in triplicate using the optical sensor conjugate in PBS (10 mM phosphate, 2.7 mM KCl, 137 mM NaCl, pH 7.4) at a 5 nM concentration (2 μM with respect to activatable oxazine). Selectivity of the optical sensor conjugate was determined by screening against a panel of biologically relevant oxidants. The integrated fluorescence response from 650 to 850 nm (λ$_{ex}$=620 nm) of the optical sensor conjugate was measured 30 min after treatment with the appropriate ROS or RNS at room temperature. The final oxidant concentration is 25 μM except for H$_2$O$_2$ (250 μM) and for the Fenton reagents (Fe(ClO$_4$)$_2$: 50 μM and H$_2$O$_2$: 250 μM) to generate HO·. Other oxidant sources include: Sodium hypochlorite (Sigma-Aldrich), peroxynitrite in 4.7% aqueous NaOH (EMD Biosciences), NOC-9 nitric oxide donor (EMD Biosciences), potassium superoxide (Strem Chemical), and 2,2'-(azobis (2-amidinopropane) dihydrochloride alkylperoxy radical source (EMD Biosciences). Photo-oxidation was investigated by placing the optical sensor conjugate under a fluorescent lamp for 2 h. For all ROS/RNS assays the final buffer pH was 7.4±0.1.

Figure 4A:
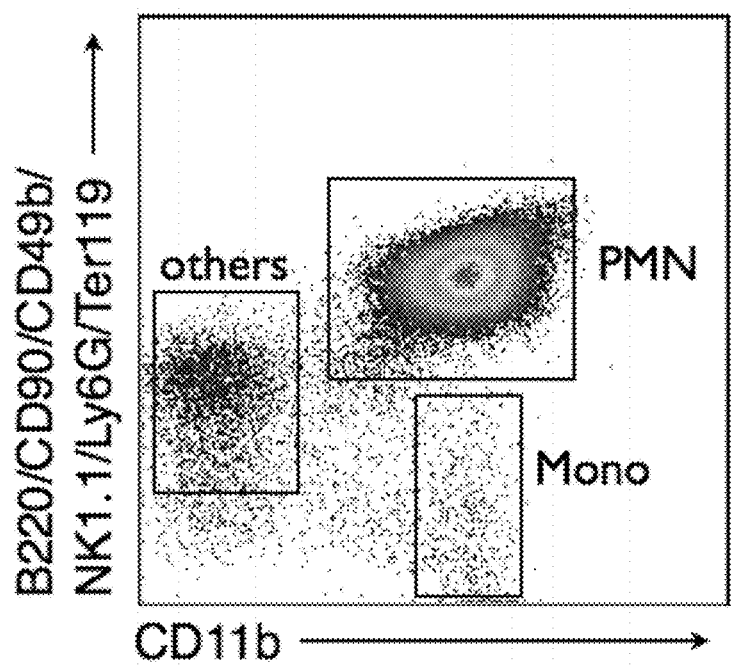
FIG. 4A is a flow cytometry image showing the ability of an optical sensor conjugate to detect HOCl generation in a mixture of living splenocytes.
Figure 4B:
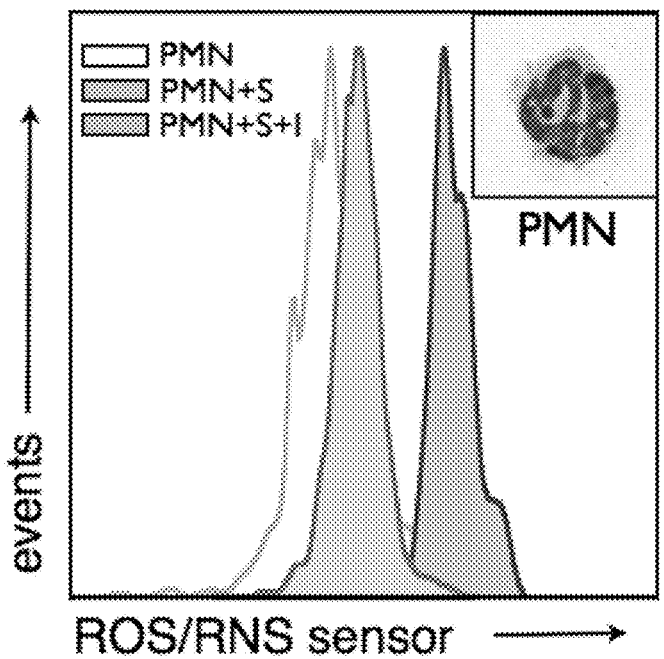
FIG. 4B is a graph showing the ability of an optical sensor conjugate to detect HOCl generation in a mixture of living splenocytes by flow cytometry.

To determine whether the optical sensor conjugate is capable of specifically monitoring MPO-dependent reactions in living cells, flow cytometry studies were performed using mouse CD11b enriched leukocytes. The flow cytometry gating strategy exploited here (FIG. 4a), namely B220/CD90/CD49b/NK1.1./Ly6G/Ter119 versus CD11b, has been used previously (Nahrendorf et al. *Circulation* 117: 379-87 (2008)). The in vivo optical sensor conjugate activation indicates that the fluorescence signal is MPO-dependent and can be blocked by peroxidase inhibition (FIG. 4b). Populations of neutrophils were confirmed by cytospin morphologic analysis after H&E staining (insets, FIG. 4b). Furthermore, HOCl generation is dominant with respect to ONOO— production in neutrophils as indicated by the ~95% reduction in MPO/ROS optical sensor conjugate activation caused by inhibiting MPO function. The compatibility of the small molecule fluorescence wavelengths with standard APC filter sets will also enable future flow cytometry studies aimed at screening for suppressors of the MPO/$H_2O_2$/Cl⁻ system in monocytes/macrophages and neutrophils.

Example 4

Isolation of Mouse Neutrophils

Flow sorting of murine neutrophils and monocyte/macrophages was performed as previously described (Nahrendorf et al. *J Exp Med* 204: 3037-47 (2007)). Briefly, spleens from euthanized mice were removed, triturated in DPBS (Lonza Inc.) at 4° C. with the end of a 3 mL syringe and filtered through 40 μm nylon mesh (BD Bioscience). Cell suspensions were centrifuged at 1500 rpm for 10 min at 4° C. Red blood cells were lysed with a hypo-osmolar ACK lysis buffer and the splenocytes were washed and resuspended in DPBS supplemented with 0.5% bovine serum albumin (BSA) and 1% fetal calf serum (FCS). Splenocytes were labeled with the following antibodies CD90-PE/53-2.1, B220-PE/RA3-6B2, CD49b-PE/DX5, NK1.1.-PE/PK136, Ly6G-PE/1A8, Ter119-PE/Ter119, CD11b-APC-Cy7/M1/70 (Antigen-Flourochrome/Clone, all from BD Bioscience) for 30 min. at 4° C. Labeled splenocytes were FACS sorted on a FACS Aria instrument (BD Bioscience) according to the expression of the myeloid marker CD11b. This CD11b⁺ enriched cell population yielded a purity of >98% myeloid cells consisting of primarily neutrophils. For morphologic characterization, sorted cells were spun, resuspended in 300 μL DPBS and prepared on glass slides by cytocentrifugation (Shandon, Inc.) at 10 G for 5 min and stained with HEMA-3 (Thermo Fisher Scientific). These CD11b⁺ enriched cells were then used in Example 5 for in vivo studies.

Example 5

In Vivo Activation of Optical Sensor Conjugates

For intracellular probe activation, 100 K of CD11b⁺-enriched cells were incubated with the optical sensor conjugate at a final concentration of 20 μM for 2 h at 4° C. Control cells were incubated in DPBS supplemented with 0.5% BSA and 1% FCS. For inhibitor studies, 4-aminobenzoic hydrazide was added at a final concentration of 10 μM. After the incubation period, cells were washed and analyzed by flow cytometry on a LSRII Cytometer (BD Bioscience) after appropriate compensations. Neutrophils were defined as $CD11b^{hi}Ly6G^{hi}$, monocyte/macrophages as $CD11b^{hi}$ $(B220/CD90/CD49b/NK1.1./Ly6G/Ter119)^{lo}$. Activation of the optical sensor conjugate was quantified in the allophycocyanine (APC) channel. Mean fluorescence intensities are shown in FIG. 4b.

To investigate the utility of the optical sensor conjugate in vivo, we determined the ability of the sensor to monitor ischemia and inflammation as a result of permanent coronary ligation in a mouse model of myocardial infarction. For all experiments, the agents (optical sensor conjugate or fluorogenic small molecule with linker) were injected intravenously into the tail-vein of the mice 12-14 hours after MI and imaged 24 hours later when neutrophil recruitment to the infarct is high. Macroscopic analysis by fluorescence reflectance imaging of coronal sections of the infarcted mouse hearts indicated that the optical sensor conjugate localized to the infarcted zone, whereas the fluorescence from the small molecule probe had washed out of the infarct and into the myocardium (FIG. 5a-h).

Microscopic analysis of tissue sections from infarcted hearts confirms that small molecule fluorescence coincides with areas rich in MPO and neutrophils, which are the dominant cells recruited early after infarction. H&E, CD11b, neutrophil and MPO staining show correlation with the oxazine signal and nanoparticle cellular localization (FIG. 6a-f). The biocompatibility of the optical sensor conjugate and its favorable pharmacokinetics will enable non-invasive fluorescence molecular tomography and other optical imaging studies to be performed to identify areas of inflammation caused by chronic disease or ischemic injury.

Example 6

Tail Vein Administration of the Optical Sensor Conjugate and Deposition/Activation in Ischemic Mouse Heart Tissue after Myocardial Infarction (MI)

Myocardial infarcts were induced in 12 mice (C57/B6, Jackson Labs) by coronary ligation during inhalation anesthesia (isoflurane 2-3% v/v+2 L/min 02) as previously described (Nahrendorf et al. *Circulation*, 113:1196-202 (2006)), with 6 mice serving as controls which did not receive coronary ligation. Anesthesized mice were intubated and a thoracotomy was performed in the 4$^{th}$ left intercostal space to visualize the left ventricle where the left coronary artery was ligated. The chest wall was closed and the mouse recovered after extubation. Approximately 12 hours following the induction of the infarct, the optical sensor conjugate was injected via tail vein as a 100-150 μL bolus (15 mg/kg). The hearts were harvested 36 hours after MI.

Hearts were excised and rinsed in PBS and cut into myocardial rings of 1-mm thickness and either immediately stained with 2-3-5-triphenyl tetrazolium chloride (TTC) (Nahrendorf et al. *Circulation*, 113:1196-202 (2006)) to highlight the infarcted tissue or used for histological analysis. Fluorescence reflectance imaging of side-by-side myocardial rings of controls and injected hearts was performed in the GFP channel ($l_{exc}$=450-480 nm with $l_{em}$ 500-530 nm) and Cy5 channel ($l_{exc}$=620-650 nm with $l_{em}$=680-710 nm) using an Olympus OV-100 system (Olympus, Center Valley, Pa.). For histology and fluorescence microscopy, the tissue was embedded in OCT medium (Sakura Finetek, Torrance, Calif.). Serial 6-μm-thick sections were collected in the midventricular level and used for immunohistochemical staining for CD11b (Abcam, Cambridge, Mass.), neutrophils (NIMP-R14, Abcam, Cambridge, Mass.) and MPO (Neo-Markers, Freemont, Calif.). The reaction was visualized as a 3-step staining procedure using biotinylated secondary antibodies (BA4001, Vector Laboratories, Burlingame, Calif.) and the AEC Substrate Kit (Vector Laboratories). Sakura Finetek Torrance, Calif.). Multichannel fluorescence microscopy was used to assess probe localization in the tissue sections with an upright epifluorescence microscope (Eclipse 80i, Nikon Instruments, Melville, N.Y.). Fluorescence microscopy images were obtained using at a green/GFP filter (Q505LP bandpass, $l_{exc}$=480±20 nm with $l_{em}$=535±25 nm) and a far-red filter (Q680LP bandpass, $l_{exc}$=650±23 nm with $l_{em}$=710±25 nm). These results indicate that the conjugates can be used to clearly image myocardial infarction in living animals.

Example 7

Synthesis of an Optical Sensor Conjugate Employing Methylene Blue

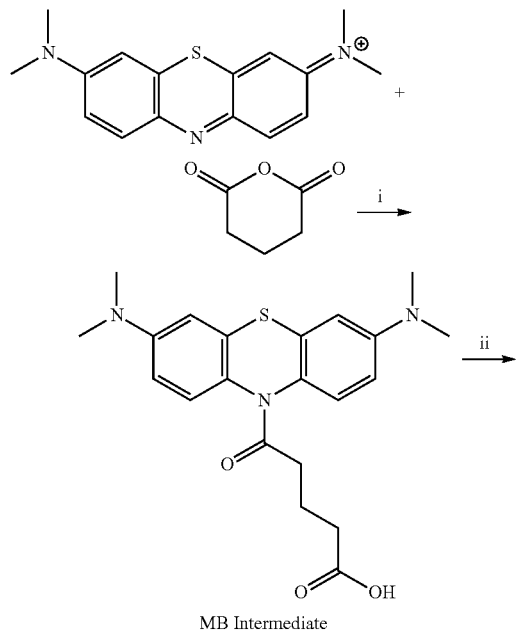

MB Intermediate

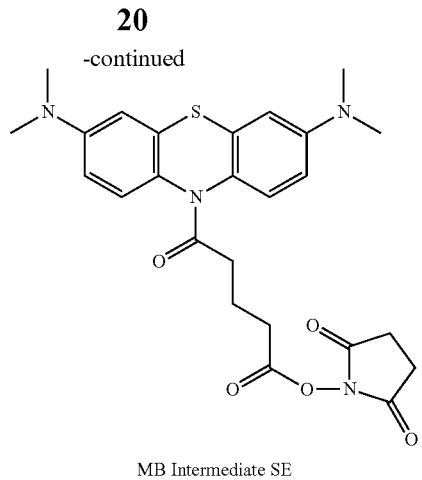

MB Intermediate SE

Synthesis of sodium 5-(3,7-bis(dimethylamino)-10H-phenothiazin-10-yl)-5-oxopentanoate (MB Intermediate, Step (i))

Methylene blue (MB, 3,7-bis(Dimethylamino)phenazathionium chloride, 0.1 mmol) was dissolved in acetonitrile (1 mL). Glutaric anhydride (1.0 mmol) and sodium hydrosulfite (0.5 mmol) were then added to the solution. The reaction mixture was then subjected to microwave irradiation with the following settings: T=150° C., t=20 minutes, power=300 Watts, Pmax=off, using a CEM Discover Microwave Model 908005. The insoluble sodium hydrosulfite was then removed by centrifugation, washing 2 times with acetonitrile, decanting off the green-colored supernatant. The crude product was then purified by preparative HPLC using a gradient from 0 to 90% acetonitrile containing 0.1% trifluoroacetic acid over 30 minutes. The product was concentrated by rotary evaporation to approximately ⅓ the original volume and the acidic solution was neutralized with 0.1 M sodium bicarbonate buffer, pH 8.0. The cloudy suspension was then loaded onto a reverse phase C18 silica-desalting column, which was then flushed with deionized water to remove excess salts before eluting the purified the MB intermediate as its sodium salt using a 1:3 mixture of acetonitrile (27% yield).

$^1$H NMR (500 MHz, CD$_3$OD) δ 7.31 (d, 2H, J=7.5 Hz), 6.81 (d, 2H, J=3.0 Hz), 6.72 (dd, 2H, J=2.5, 9.0 Hz), 2.95 (s, 12H), 2.49 (broad s, 2H), 2.25 (t, 2H, J=7.0 Hz), 1.82 (pentet, 2H, J=7.5 Hz) ESI-MS [M+H]$^+$ (m/z) calcd. for C21H26N3O3S$^+$; 400.17 m/z, found 400.2 m/z.

Synthesis of 2,5-dioxopyrrolidin-1-yl 5-(3,7-bis (dimethylamino)-10H-phenothiazin-10-yl)-5-oxo-pentanoate (MB Intermediate SE, Step (ii))

N,N'-disuccinimidyl carbonate (70 μmol) and diisopropylethylamine (70 μmol) were added to a solution of the MB intermediate (17 μmol) in 1 mL of DMSO. This reaction mixture was allowed to stir at room temperature for 1 hour or until completion as determined by consumption of the starting material using LCMS. The title product was identified by a new peak in the LC trace slightly more non-polar than the starting material with a corresponding mass of 497.3 (ESI MS [M+H]$^+$ (m/z) calcd. for C$_{25}$H$_{29}$N$_4$O$_5$S$^+$; 497.18).

Synthesis of the MB Optical Sensor Conjugate

CLIO nanoparticles (5 mg Fe) were added directly to the crude MB intermediate SE reaction mixture from above after completion (17 μmol product if quantitative), followed by the addition of 1 mL of DMSO and 3 mL sodium phosphate buffer (10 mM, pH 8.0). This solution was then allowed to stir overnight in the dark at room temperature. The MB intermediate conjugated nanoparticles were then purified by size exclusion chromatography (Sephadex G-25 resin) eluting with PBS, pH 7.4. This purified nanoparticle solution was then concentrated using an Amicon Ultra 5K MWCO centrifugal filter. The nanoparticle concentration was determined by comparing the absorbance at 400 nm to a known unmodified CLIO dilution. The number of quenched methylene blue fluorophores per nanoparticle was then determined by release of the fluorophore by activation with excess HOCl. The extinction coefficient at 664 nm ($\varepsilon$=74,000 $M^{-1}$ $cm^{-1}$ in water) was used to calculate the amount of fluorophore released. This yielded approximately 70 activatable methylene blue groups per nanoparticle.

Example 8

Synthesis of an Optical Sensor Conjugate Employing 8-Hydroxyjulolidine

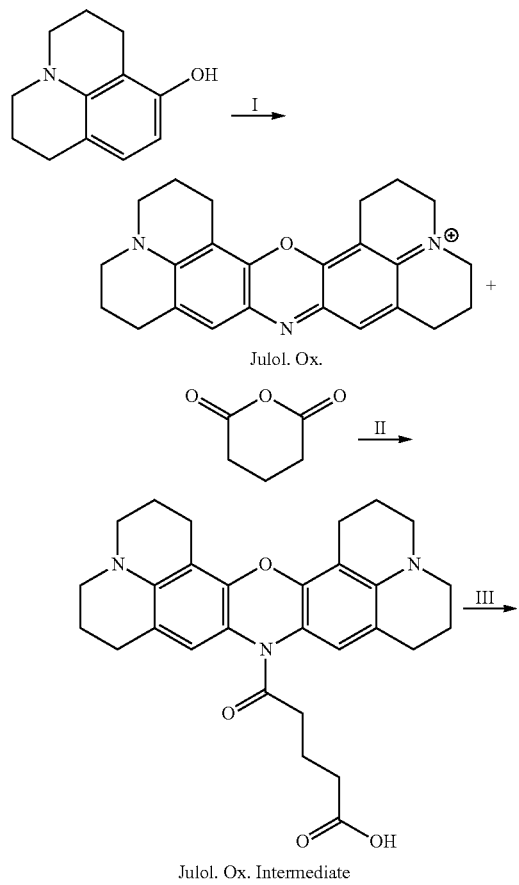

Julol. Ox. Intermediate

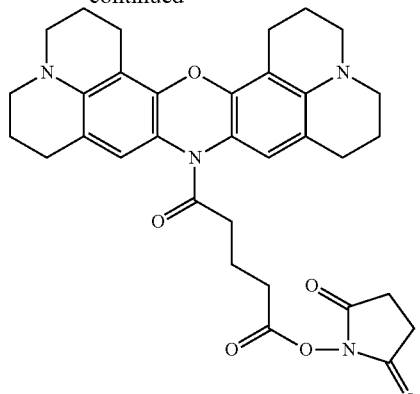

Julol. Ox. Intermediate SE

Synthesis of 2,3,6,7,12,13,16,17-Octahydro-1H,5H,11H,15H-diquinolizino[1,9-bc:1',9'-hi]phenoxazin-4-ium chloride (Julol. Ox., Step (I))

Sodium nitrite (4 mmol) dissolved in water was added dropwise to 8-hydroxyjulolidine (8 mmol) stirring in acetic acid on ice. The now brownish solution was then stirred for 30 minutes before heating to 65° C. for 4 hours. The acetic acid was then removed from the dark blue solution by rotary evaporation and the title product as its trifluoroacetate salt was purified by HPLC using a gradient from 25 to 90% acetonitrile containing 0.1% trifluoroacetic acid over 30 min. HPLC fractions containing the product were concentrated by rotary evaporation and loaded onto a reverse phase C18 column and washed with 250 mL 0.1% HCl to exchange the trifluoroacetate counteranion for chloride. The chloride salt of the title compound was then eluted with 50% acetonitrile in water and lyophilized to give a dark blue powder (25% yield). ESI-MS $[M]^+$ (m/z) calcd. for $C_{24}H_{26}N_3O^+$; 372.21, found 372.3.

Synthesis of sodium 5-(2,3,6,7,12,13,16,17-octahydro-1H-diquinolizino[1,9-bc:1',9'-hi]phenoxazin-9(5H,11H,15H)-yl)-5-oxopentanoate (Julol. Ox. Intermediate, Step (II))

Julol. Ox. (0.1 mmol) and glutaric anhydride (1 mmol) were dissolved in 2 mL dichloroethane in a thick-walled pressure tube. Triethylamine (2 mmol) was then added before sealing the tube and heating to 125° C. for approximately 15 minutes or until the visible blue color disappears and the solution becomes dark brown. The solvent was removed by rotary evaporation and the title compound was purified by HPLC after redissolving the brown solid in DMF using a gradient from 0 to 90% acetonitrile containing 0.1% trifluoroacetic acid over 30 minutes. The product fractions were concentrated by rotary evaporation to approximately ⅓ the original volume and the acidic solution was neutralized with 0.1 M sodium bicarbonate buffer, pH 8.0. The cloudy suspension was then loaded onto a reverse phase C18 silica-desalting column, which was then flushed with deionized water to remove excess salts before eluting the purified Julol. Ox. intermediate as its sodium salt using a 1:1 mixture of acetonitrile:water that was lyophilized to dryness (42% yield). ESI MS $[M+H]^+$ (m/z) calcd. for $C_{29}H_{34}N_3O_4^+$; 488.25, found 488.3.

Synthesis of 2, 5-dioxopyrrolidin-1-yl 5-(2,3,6,7,12, 13,16,17-octahydro-1H-diquinolizino[1,9-bc:1',9'-hi] phenoxazin-9(5H,11H,15H)-yl)-5-oxopentanoate (Julol. Ox. Intermediate SE, Step (III))

Julol. Ox. intermediate (0.04 mmol) and N,N'-disuccinimidyl carbonate (0.16 mmol) were dissolved in 2 mL of DMSO. Diisoproplyethylamine (16 mmol) was then added and the solution was allowed to stir at room temperature for 1 hour or until completion as determined by complete consumption of the starting material using LCMS. The title product was identified by a new peak in the LC trace slightly more non-polar than the starting material with a corresponding mass of 585.4 (ESI MS [M+H]$^+$ (m/z) calcd. for $C_{33}H_{37}N_4O_6^+$; 585.27).

Nanoparticle Conjugation of Julol. Ox. Intermediate SE

CLIO nanoparticles (5 mg Fe) were added directly to the crude Julol. Ox. intermediate SE reaction mixture from above (40 μmol product if quantitative), followed by the addition of 2.5 mL of DMSO and 1.8 mL PBS, pH 7.4. This solution was then allowed to mix overnight in the dark at room temperature. The Julol. Ox. intermediate conjugated nanoparticles were then purified by size exclusion chromatography (Sephadex G-25 resin) eluting with PBS, pH 7.4. This purified nanoparticle solution was then concentrated using an Amicon Ultra 5K MWCO centrifugal filter. The nanoparticle concentration was determined by comparing the absorbance at 400 nm to a known unmodified CLIO dilution. An estimated number of quenched Julol. Ox. per nanoparticle was then determined by release of the fluorophore by activation with excess HOCl. The approximate extinction coefficient at 675 nm ($\varepsilon$=100,000 M$^{-1}$ cm$^{-1}$ in PBS) was used to calculate the amount of fluorophore released. This yielded 40 activatable Julol. Ox. groups per nanoparticle.

Example 9

Figure 7A:
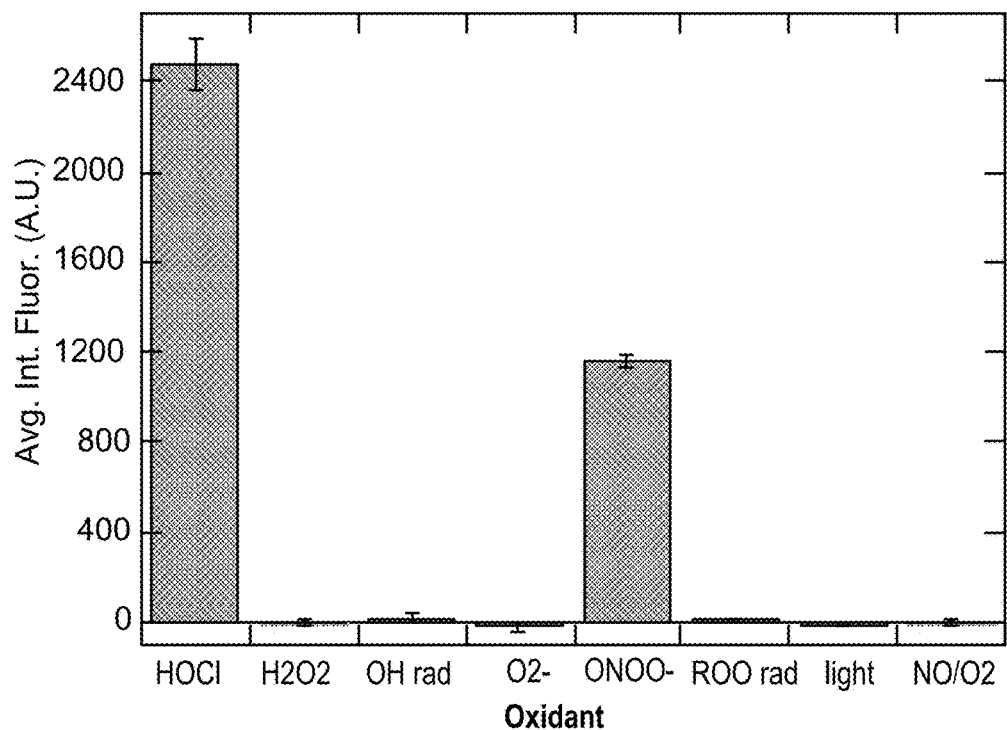
FIG. 7A is a bar graph showing fluorescence response of Methylene Blue optical sensor conjugates with various oxidants.
Figure 7B:
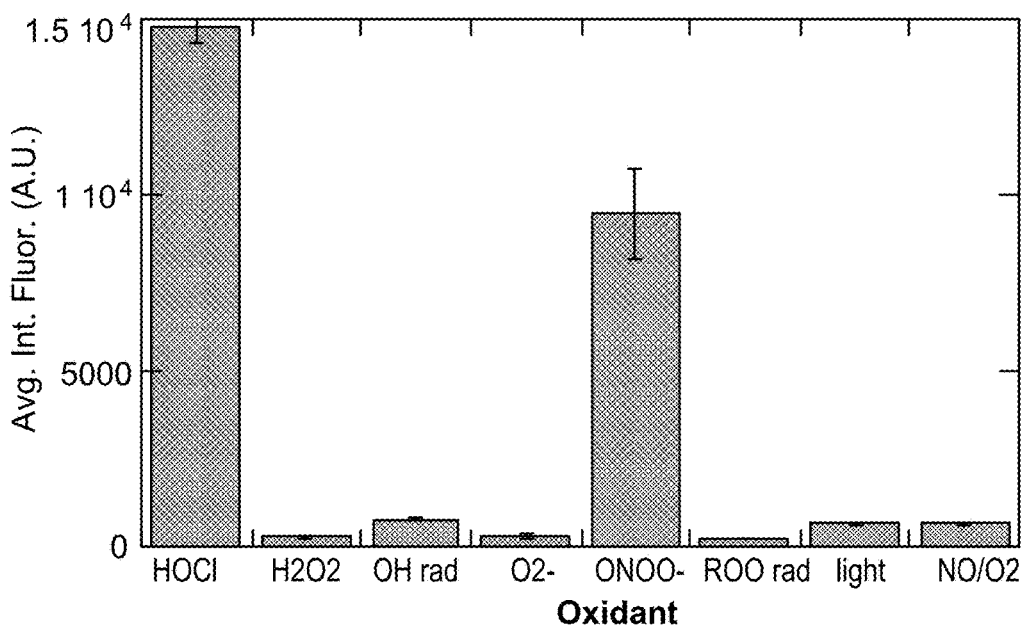
FIG. 7B is a bar graph showing fluorescence response of Julol. Ox. optical sensor conjugates with various oxidants.

Oxidant Activation Assays of MB Optical Sensor Conjugates and Julol. Ox. Optical Sensor Conjugates The quenched dye functionalized nanoparticles were then subjected to screening with a panel of biologically relevant reactive oxygen and reactive nitrogen species (ROS/RNS). Assays were performed in triplicate in PBS buffer containing 10 mM phosphate, 2.7 mM KCl, 137 mM NaCl pH 7.4. The amount of nanoparticle used was such that the final concentration of fluorophore would be 2 μM upon complete activation. The integrated fluorescence response from 665-850 nm ($\lambda_{ex}$=640 nm) for methylene blue and from 675-850 nm ($\lambda_{ex}$=650 nm) for Julol. Ox. was measured after treatment with the individual ROS/RNS for 30 minutes at room temperature. The final oxidant concentration was 25 μM with the exception of H$_2$O$_2$ (250 μM) and the Fenton reagents (Fe(ClO$_4$)$_2$: 50 μM and H$_2$O$_2$: 250 μM) used to generate HO·. Photo-oxidation was investigated by placing the functionalized nanoparticles under fluorescent light for 2 hours. The results of these assays can be seen in FIGS. 7a and 7b. Both the MB and Julol. Ox. optical sensor conjugates showed specificity toward the ROS/RNS, HOCl and ONOO—.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for detecting reactive oxygen, reactive nitrogen, or both in a subject, the composition comprising a fluorogenic small molecule and a particle, wherein the fluorogenic small molecule comprises a compound of Formula I:

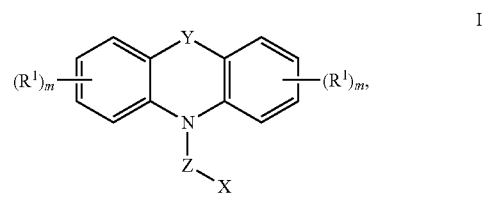

or a salt thereof, wherein:
Z is a linker and comprises $C_{3-20}$ alkyl, wherein any of the carbons in $C_{3-20}$ alkyl can be replaced with —C(O)—, C(O)O—, —C(O)NR$^A$—, —C(NH)—, oxygen, sulfur, —SO$_2$—, —NR$^A$SO$_2$——NR$^a$—;
X is selected from

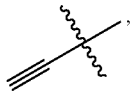

N$_3$, C(O)Cl, and C(O)OR$^A$;
Y is selected from O, S, Se, Te, N(R$^A$), and C(Me)$_2$;
R$^1$ is NR$^C$R$^D$; or 2 or 3 R$^1$ adjacent to each other and together with the C atoms to which they are attached form 1 or 2 heterocycloalkyl, optionally substituted by 1, 2, 3, or 4 substituents independently selected from H, OH, C$_{1-6}$ alkyl, OR$^A$, C(O)R$^B$, C(O)NR$^C$R$^D$, and C(O) OR$^A$;
R$^A$, R$^B$, R$^C$ and R$^D$ are independently selected from H, C$_{1-6}$ alkyl, and succinimidyl; and m is 1, 2, 3, or 4.

2. The composition of claim 1, wherein the particle further comprises a reporting agent.

3. The composition of claim 1, wherein the fluorogenic small molecule is selected from:

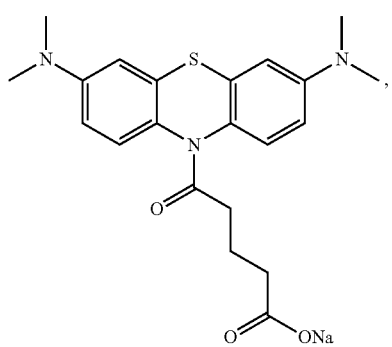

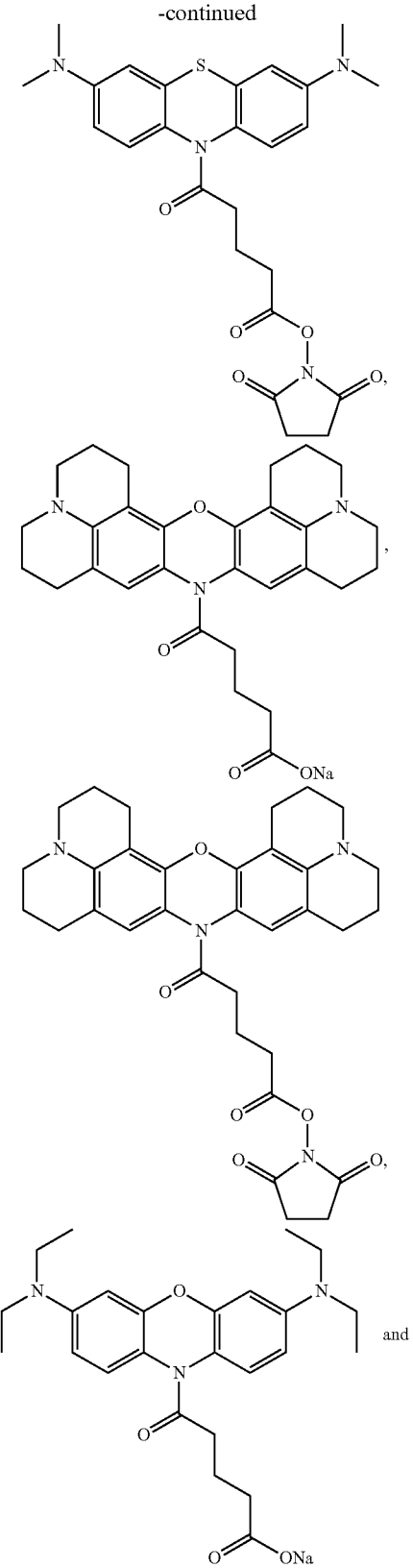

4. The composition of claim 1, wherein X is C(O)OR$^A$ and Y is O.

5. The composition of claim 1, wherein R$^1$ is NR$^C$R$^D$.

6. The composition of claim 1, wherein the fluorogenic small molecule is or a salt thereof.

7. The composition of claim 1, wherein the reactive oxygen, reactive nitrogen, or both are associated with inflammation.

8. The composition of claim 7, wherein the inflammation is associated with tissue injury.

9. The composition of claim 1, wherein the reactive oxygen, reactive nitrogen, or both are associated with Alzheimer's disease, atherosclerosis, cancer, stroke, inflammatory bowel disease, or organ transplantation.

10. The composition of claim 1, wherein 2 or 3 R$^1$ adjacent to each other and together with the C atoms to which they are attached form 1 or 2 heterocycloalkyl, optionally substituted by 1, 2, 3, or 4 substituents independently selected from H, OH, C$_{1-6}$ alkyl, OR$^A$, C(O)R$^B$, C(O)NR$^C$R$^D$, and C(O)OR$^A$.

* * * * *

UNITED STATES PATENT AND TRADEMARK OFFICE
CERTIFICATE OF CORRECTION

PATENT NO. : 10,357,574 B2  
APPLICATION NO. : 15/583197  
DATED : July 23, 2019  
INVENTOR(S) : Scott A. Hilderbrand et al.

Page 1 of 1

It is certified that error appears in the above-identified patent and that said Letters Patent is hereby corrected as shown below:

On the Title Page

Column 1 (Related U.S. Application Data), Line 1, delete "Continuation" and insert -- Division --

Column 2 item (56) (Other Publications), Line 16, delete "(Apr. 19," and insert -- (Apr. 29, --

In the Claims

In Column 24, Line 28 (approx.), Claim 1, delete "—$NR^ASO_2$——$NR^a$—;" and insert -- —$NR^ASO_2$— —$NR^A$—; --

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*